(12) United States Patent
Swanson et al.

(10) Patent No.: US 6,445,939 B1
(45) Date of Patent: Sep. 3, 2002

(54) ULTRA-SMALL OPTICAL PROBES, IMAGING OPTICS, AND METHODS FOR USING SAME

(75) Inventors: Eric Swanson, Acton; Christopher L. Petersen, Carlise; Edward McNamara, Chelmsford, all of MA (US); Ronald B. Lamport, Pelham, NH (US); David L. Kelly, Westford, MA (US)

(73) Assignee: LightLab Imaging, LLC, Westford, MA (US)

( * ) Notice: Subject to any disclaimer, the term of this patent is extended or adjusted under 35 U.S.C. 154(b) by 0 days.

(21) Appl. No.: 09/370,756

(22) Filed: Aug. 9, 1999

(51) Int. Cl.$^7$ .................................................. A61B 5/00
(52) U.S. Cl. ........................ 600/342; 600/434; 385/33; 385/34
(58) Field of Search ................................ 356/450–453; 385/32–39, 12, 28, 96; 600/435, 325, 327, 433, 434, 342–343, 332; 604/96.01

(56) References Cited

U.S. PATENT DOCUMENTS

| | | | |
|---|---|---|---|
| 3,532,037 A | 10/1970 | Neuilly | 95/11 |
| 3,549,239 A | 12/1970 | Brienza et al. | 350/162 |

(List continued on next page.)

FOREIGN PATENT DOCUMENTS

| | | | | |
|---|---|---|---|---|
| DE | 3527245 | 2/1987 | ............ | G01B/11/02 |
| DE | 3627420 A1 | 2/1987 | ............ | G02B/26/10 |
| DE | 4309056 | 9/1994 | ............ | G01B/9/02 |
| EP | 60265005 | 11/1985 | ............ | G01B/11/24 |
| EP | 04135552 | 5/1992 | ............ | G01B/11/24 |
| EP | 0501034 A1 | 9/1992 | ............ | A61F/9/00 |
| EP | 0 825 464 A1 | 2/1998 | | |
| EP | 0825464 A1 | 2/1998 | ............ | G02B/6/42 |
| FR | 2 734 914 | 12/1996 | | |
| FR | 2734914 A1 | 12/1996 | ............ | G02B/6/32 |
| GB | 2191855 A | 12/1987 | ............ | G01N/21/84 |
| GB | 8611055 | 12/1987 | | |
| JP | 6-35946 | 5/1994 | ............ | G01N/21/27 |
| WO | 92/14399 | 9/1992 | ............ | A61B/5/00 |
| WO | 92/19930 | 11/1992 | ............ | G01B/9/02 |
| WO | 95/33970 A | 12/1995 | ............ | G01B/9/02 |
| WO | WO 97/32182 | 9/1997 | | |
| WO | 97/32182 | 9/1997 | | |
| WO | 97/41767 | 11/1997 | | |
| WO | 98/27865 | 7/1998 | ............ | A61B/5/05 |
| WO | 98/38907 | 11/1998 | ............ | A61B/5/00 |
| WO | 00/42906 | 7/2000 | ............ | A61B/5/00 |

OTHER PUBLICATIONS

Adamson, et al., "A new wave guide for use with a $CO_2$ delivery system for laparoscopic surgery", *The Journal of Reproductive Medicine*, pp. 875–878 (Nov. 13–17, 1991).

Bail et al., "Optical coherence tomography with the "Spectral Radar"–Fast optical analysis in volume scatters by short coherence interferometry", *Proceedings of the European Biomedical Optics, BiOS Europe '96*, paper 2925–2930, Vienna, Austria.

(List continued on next page.)

Primary Examiner—Eric F. Winakur
Assistant Examiner—Matthew J Kremer
(74) Attorney, Agent, or Firm—Testa, Hurwitz & Thibeault, LLP

(57) ABSTRACT

Ultra-small optical probes comprising a single-mode optical fiber and a lens which has substantially the same diameter as the optical fiber. The optical fiber and lens are positioned in a probe housing which is in the form of an insertional medical device such as a guidewire. Connector elements are provided to facilitate the attachment of the probe to an optical system and the quick disconnection of the probe from the optical system. The probe is used to obtain optical measurements in situ in the body of an organism and can be used to guide interventional procedures by a surgeon.

11 Claims, 12 Drawing Sheets

U.S. PATENT DOCUMENTS

| | | | |
|---|---|---|---|
| 3,556,079 A | 1/1971 | Omizo | |
| 3,710,798 A | 1/1973 | Bredemeier | |
| 3,769,963 A | 11/1973 | Goldman et al. | |
| 3,821,510 A | 6/1974 | Muncheryan | 219/121 L |
| 3,905,703 A | 9/1975 | Matsumoto | 356/106 R |
| 3,906,953 A | 9/1975 | Wallace et al. | |
| 3,961,621 A | 6/1976 | Northeved | |
| 3,961,841 A | 6/1976 | Giordmaine | 350/160 R |
| 4,058,114 A | 11/1977 | Soldner | |
| 4,091,814 A | 5/1978 | Togo | 128/303.1 |
| 4,141,362 A | 2/1979 | Wurster | 128/303.1 |
| 4,171,159 A | 10/1979 | White | 356/349 |
| 4,336,809 A | 6/1982 | Clark | 128/665 |
| 4,420,260 A | 12/1983 | Martinelli | 356/351 |
| 4,545,390 A | 10/1985 | Leary | 128/772 |
| 4,554,929 A | 11/1985 | Samson et al. | 128/772 |
| 4,596,466 A | 6/1986 | Ulrich | 356/345 |
| 4,597,755 A * | 7/1986 | Samson et al. | 604/103 |
| 4,612,938 A | 9/1986 | Dietrich et al. | 128/665 |
| 4,619,274 A | 10/1986 | Morrison | 128/772 |
| 4,638,800 A | 1/1987 | Michel | 128/303.1 |
| 4,648,892 A | 3/1987 | Kittrell et al. | 65/4.21 |
| 4,652,129 A | 3/1987 | Martinelli | 356/345 |
| 4,669,465 A | 6/1987 | Moore et al. | 128/303.1 |
| 4,669,467 A | 6/1987 | Willett et al. | 128/303.1 |
| 4,718,417 A | 1/1988 | Kittrell et al. | 128/303.1 |
| 4,721,117 A | 1/1988 | Mar et al. | 128/772 |
| 4,748,986 A | 6/1988 | Morrison et al. | 128/772 |
| 4,796,994 A | 1/1989 | Bager | 356/358 |
| 4,819,632 A | 4/1989 | Davies | 128/303.1 |
| 4,834,102 A | 5/1989 | Schwarzchild et al. | 128/662.06 |
| 4,844,062 A | 7/1989 | Wells | 128/303.1 |
| 4,873,989 A | 10/1989 | Einzig | 128/692 |
| 4,887,606 A | 12/1989 | Yock et al. | |
| 4,899,733 A | 2/1990 | DeCastro et al. | 128/7 |
| 4,900,314 A | 2/1990 | Quackenbush | 604/282 |
| 4,913,142 A | 4/1990 | Kittrell et al. | 606/7 |
| 4,928,005 A | 5/1990 | Lefevre et al. | 250/227.23 |
| 4,958,930 A | 9/1990 | Robertson, Jr. | 356/357 |
| 4,969,736 A | 11/1990 | Slotwinski | 356/4.5 |
| 5,005,584 A | 4/1991 | Little | 128/748 |
| 5,032,722 A | 7/1991 | Boesl et al. | 250/287 |
| 5,034,613 A | 7/1991 | Denk et al. | 250/458.1 |
| 5,039,193 A * | 8/1991 | Snow et al. | 385/25 |
| 5,053,033 A | 10/1991 | Clarke | 606/3 |
| 5,094,534 A | 3/1992 | Cole et al. | 356/345 |
| 5,104,392 A | 4/1992 | Kittrell et al. | 606/15 |
| 5,106,387 A | 4/1992 | Kittrell et al. | 606/15 |
| 5,110,211 A | 5/1992 | Niki et al. | 326/346 |
| 5,114,403 A | 5/1992 | Clarke et al. | 604/96 |
| 5,133,598 A | 7/1992 | Badeau | 356/345 |
| 5,155,549 A | 10/1992 | Dhadwal | 356/336 |
| 5,157,457 A | 10/1992 | Taylor | 356/345 |
| 5,196,004 A | 3/1993 | Sinofsky | 606/3 |
| 5,197,470 A | 3/1993 | Helfer et al. | 128/634 |
| 5,201,317 A | 4/1993 | Kanazawa et al. | 128/665 |
| 5,202,745 A | 4/1993 | Sorin et al. | 356/73.1 |
| 5,217,456 A | 6/1993 | Narciso, Jr. | 606/15 |
| 5,251,198 A | 10/1993 | Strickler | 369/110 |
| 5,257,991 A | 11/1993 | Fletcher et al. | 606/17 |
| 5,267,340 A * | 11/1993 | Pan | 385/123 |
| 5,268,738 A | 12/1993 | Baney et al. | 356/345 |
| 5,268,741 A | 12/1993 | Chou et al. | 356/345 |
| 5,291,267 A | 3/1994 | Sorin et al. | 356/345 |
| 5,303,026 A | 4/1994 | Strobl et al. | 356/318 |
| 5,305,759 A | 4/1994 | Kaneko et al. | |
| 5,318,024 A | 6/1994 | Kittrell et al. | 128/634 |
| 5,321,501 A | 6/1994 | Swanson et al. | 356/345 |
| 5,325,177 A | 6/1994 | Peterson | 356/357 |
| 5,343,543 A | 8/1994 | Novak, Jr. et al. | 385/31 |
| 5,354,294 A | 10/1994 | Chou | 606/16 |
| 5,365,335 A | 11/1994 | Sorin | 356/345 |
| 5,366,456 A | 11/1994 | Rink et al. | 606/16 |
| 5,370,649 A | 12/1994 | Gardetto et al. | 606/17 |
| 5,383,467 A | 1/1995 | Auer et al. | |
| 5,390,023 A | 2/1995 | Biegen | 356/359 |
| 5,401,270 A | 3/1995 | Müller et al. | 606/13 |
| 5,421,337 A | 6/1995 | Richards-Kortum et al. | |
| 5,421,339 A | 6/1995 | Ramanujam et al. | |
| 5,428,699 A | 6/1995 | Pon | 385/31 |
| 5,434,669 A | 7/1995 | Tabata et al. | 356/345 |
| 5,439,000 A | 8/1995 | Gunderson et al. | |
| 5,459,570 A | 10/1995 | Swanson et al. | 356/345 |
| 5,465,147 A | 11/1995 | Swanson | 356/345 |
| 5,486,701 A * | 1/1996 | Norton et al. | 250/372 |
| 5,490,521 A | 2/1996 | Davis et al. | |
| 5,495,541 A | 2/1996 | Murray et al. | 385/33 |
| 5,501,226 A | 3/1996 | Petersen et al. | 128/691 |
| 5,501,599 A | 3/1996 | Rechmann | 433/215 |
| 5,509,917 A | 4/1996 | Cecchetti et al. | 606/15 |
| 5,537,499 A | 7/1996 | Brekke | 385/31 |
| 5,555,087 A | 9/1996 | Miyagawa et al. | 356/345 |
| 5,562,100 A | 10/1996 | Kittrell et al. | |
| 5,562,657 A | 10/1996 | Griffin | 606/17 |
| 5,570,182 A | 10/1996 | Nathel et al. | 356/345 |
| 5,571,099 A | 11/1996 | Purcell, Jr. et al. | 606/17 |
| 5,589,938 A | 12/1996 | Deck | 356/359 |
| 5,601,087 A | 2/1997 | Gunderson et al. | |
| 5,612,540 A | 3/1997 | Richards-Kortum et al. | 250/461.2 |
| 5,623,932 A | 4/1997 | Ramanujam et al. | |
| 5,697,373 A | 12/1997 | Richards-Kortum et al. | |
| 5,699,795 A | 12/1997 | Richards-Kortum et al. | |
| 5,715,825 A | 2/1998 | Crowley | |
| 5,748,598 A | 5/1998 | Swanson et al. | 369/94 |
| 5,752,518 A | 5/1998 | McGee et al. | |
| 5,762,613 A | 6/1998 | Sutton et al. | 600/564 |
| 5,772,657 A | 6/1998 | Hmelar et al. | 606/15 |
| 5,784,352 A | 7/1998 | Swanson et al. | 369/94 |
| 5,787,890 A | 8/1998 | Reiter et al. | 128/665 |
| 5,815,611 A | 9/1998 | Dhadwal | 385/12 |
| 5,872,879 A * | 2/1999 | Hamm | 385/25 |
| 5,921,926 A | 7/1999 | Rolland et al. | 600/407 |
| 6,041,156 A * | 3/2000 | Heitmann | 385/139 |
| 6,057,952 A * | 5/2000 | Kubo et al. | 359/196 |
| 6,111,645 A | 8/2000 | Tearney et al. | 356/354 |
| 6,130,972 A * | 10/2000 | Shiraishi et al. | 385/33 |
| 6,134,003 A * | 10/2000 | Tearney et al. | 356/450 |
| 6,160,826 A | 12/2000 | Swanson et al. | 372/20 |
| 6,253,004 B1 * | 6/2001 | Lee et al. | 385/31 |
| 2001/0001814 A1 * | 5/2001 | Estabrook et al. | |

OTHER PUBLICATIONS

Bail, M. et al., "Optical coherence tomography by "spectral radar" for the analysis of human skin", *SPIE*, vol. 3196, 1997.

Bauer, O. et al., "Small diameter laparoscopy using a microlaparoscope", *Human Reproduction*, vol. 10, No. 6, pp. 1461–1464 (1995).

Beaud, P. et al. "Optical reflectometry with micrometer resolution for the investigation of integrated optical devices", *IEEE Journal of Quantum Electronics*, vol. 25, No. 4, pp. 755–759 (Apr. 4, 1989).

Bouma, B. et al., "High–resolution optical coherence tomographic imaging using a mode–locked Ti:Al₂O₃ laser source", *Optics Letters*, vol. 22, No. 13, pp. 1486–1488 (Jul. 1, 1995).

Brezenski, Mark E., et al., "Optical Coherence Tomography for Optical Biopsy Properties and Demonstration of Vascular Pathology", *Circulation*, vol. 93, No. 6, pp. 1206–1213 (Mar. 15, 1996).

Brezinski, M. E., et al. "Imaging of coronary artery microstructure (in vitro) with optical coherence tomography", *The American Journal of Cardiology*, vol. 77 (Jan. 1, 1996).

Chinn, S. R. and E. A. Swanson, "Blindness limitations in optical coherence domain reflectometry", *Electronics Letters*, vol. 29, No. 23, pp. 2025–2027 (Nov. 11, 1993).

Chinn, S.R. and E. A. Swanson, "Optical Coherence Tomography Using a Frequency–Tunable Optical Source", *Optics Letters*, vol. 22, No. 5, pp. 340–342 (Mar. 1, 1997).

Chornenky, V. "Low–coherence interferometry in coronary arteries", *Coronary Artery Disease*, vol. 6, No. 5, pp. 377–380 (May 1995).

Clivaz, X. et al. "High Resolution reflectometry in biological tissues", *Optics Letters*, vol. 17, No. 1, pp. 4–6 (Jan. 1, 1992).

Clivaz, X., et al. "1.5 μm Resolution optical low coherence reflectometry in biological tissues", *SPIE Proc.*, vol. 2083, No. 19, pp. 1–9 (1994).

Danielson, B. and C. Wittenberg "Guided–wave reflectometry with micrometer resolution", *Applied Optics*, vol. 26, No. 14, pp. 2836–2842 (Jul. 15, 1987).

De Souza, E. et al. "Spectrally sliced WDM using a single femtosecond source", *Applied Optics*, vol. 34, No. 25, pgs.

Dickensheets, D. L., et al., "Micromachined scanning confocal optical microscope", *Optics Letters*, vol. 21, No. 10, pp. 764–766 (May 15, 1996).

Decker–Dunn, et al., "Multifiber gradient–index lens laser angioplasty probe", *Lasers in Surgery and Medicine*, vol. 10, pp. 85–93 (1990).

Edelstein, D.C. et al., "Rapid programmable 300ps optical delay scanner and signal–averaging system for ultrafast measurements", *Rev. Sci. Instrum*, vol. 62, No. 3, pp. 579–583 (1991).

Eigensee, A., et al., "A new method of short–coherence–interferometry in human skin (in vivo) and in solid volume scatterers", *European Biomedical Optics Week, BIOS '96*, pp. 2930–2928 (1996).

Evans, J. L. et al., "Arterial Imaging with a new Forward–Viewing Intravascular Ultrasound Catheter, I Initial Studies", *Circulation*, vol. 89, No. 2, pp. 712–717 (Feb. 1994).

Fercher, A. et al."Eye–length measurement by interferometry with partially coherent light", *Optics Letters*, vol. 13, No. 3, pp. 186–188 (Mar. 1988).

Fercher, Adolf F., "Optical Coherence Tomography", *Journal of Biomedical Optics*, vol. 1, No. 2, pp. 157–173 (Apr. 1996).

Fork, et al., "Real–time intensity autocorrelation interferometer", *Applied Optics*, vol. 17, No. 22, pp. 3534–3535 (Nov. 15, 1978).

Gelikonov, V. et al. "Coherent optical tomography of microscopic inhomogeneities in biological tissues", *JETP*, vol. 61, No. 2, pp. 158–162 (Jan. 25, 1995).

Gilgen, H. et al. "Submillimeter Optical Reflectometry", *Journal of Lightwave Technology*, vol. 7, No. 8, pp. 1225–1233 (Aug. 1989).

Giniunas, L. et al., "Endoscope with optical sectioning capability", *Applied Optics*, vol. 32, No. 16, pp. 2888–2890 (Jun. 1, 1993).

Gmitro, A. F. and D. Aziz, "Confocal microscopy through a fiber–optic imaging bundle", *Optics Lettes*, vol. 18, No. 8, pp. 565–567 (Apr. 15, 1993).

Goldberg, B. B. et al., "Sonographically Guided Laparoscopy and Mediastinoscopy Using Miniature Catheter–Based Transducers", *Journal of Ultrasound Medicine*, vol. 12, pp. 49–54 (1993).

Haberland, U. et al., "Investigation of highly scattering media using near–infrared continuous wave tunable semiconductor laser", *SPIE Proceedings*, vol. 2389, pp. 1–10 (1995).

Hammer, D. X. et al., "Intraocular laser surgical probe for membrane disruption by laser–induced breakdown", *Applied Optics*, vol. 36, No. 7, pp. 1684–1693 (Mar. 1, 1997).

He, Z. et al., "Selective image extraction by synthesis of the coherence function using two–dimensional optical lock–in amplifier with microchannel spatial light modulator", *IEEE Photonics Technology Letters*, vol. 9, No. 4, pp. 514–516 (Apr. 1997).

Hee, M. et al. "Quantitative assessment of macular edema with optical coherence tomography", *Archives of Ophthalmology*, vol. 113, pp. 1019–1029 (Aug. 1995).

Hee, M. et al., "Polarization–sensitive low–coherence reflectometer for birefringence characterization and ranging", *Journal Optical Society of America B*, vol. 9, No. 6, pp. 903–908 (Jun. 1992).

Heritage, J.P. et al., "Picosecond pulse shaping by spectral phase and amplitude manipulation", *Optics Letter*, vol. 10, No. 12, pp. 609–611 (Dec. 1985).

Hillegas, C. W., et al., "Femtosecond laser pulse shaping by use of microsecond radio–frequency pulses", *Optics Letters*, vol. 19, No. 10 (May 15, 1994).

Hitzenberger, C. "Optical measurement of the axial eye length by laser doppler interferometry", *Investigative Ophthalmology & Visual Science*, vol. 32, No. 3, pp. 616–624 (Mar. 3, 1991).

Hitzenberger, C. K. et al., "Measurement of Corneal Thickness by Laser Doppler Interferometry", *Investigative Opthalmology & Visual Science*, vol. 33, No. 1, pp. 98–103 (Jan. 1, 1992).

Huang, D. et al. "Micron–resolution ranging of cornea anterior chamber by optical reflectometry", *Lasers in Surgery and Medicine*, vol. 11, pp. 419–425 (May 10, 1991).

International Search Report PCT/US00/01228 (8 pgs).

Izatt, J. "Micrometer–scale resolution imaging of the anterior eye in vivo with optical coherence tomography", *Archives of Opthalmology*, vol. 112, pp. 15841589 (Dec. 1994).

Izatt, J. A. et al. "Optical coherence microscopy in scattering media", *Optics Letters*, vol. 19, No. 8, pp. 590–592 (Apr. 15, 1994).

Kinsel et al. "Design and Calibration of an Electrostatic Energy Analyzer–Time–of–Flight Mass Spectrometer for Measurement of Laser–Desorbed Ion Kenetic Energies", *Journal American Society for Mass Spectrometry*, vol. 6, pp. 619–622 (1995).

Kobayashi, M. et al. "Optical fiber component characterization by high–intensity and high–spatial–resolution interferometric optical–time–domain reflectometer", *IEEE Photonics Technology Letters*, vol. 3, No. 6, pp. 564–566 (Jun. 6, 1991).

Kobayashi, M. et al. "Polarization–independent interferometric optical–time–domain reflectometer", *Journal of Lightwave Technology*, vol. 9, No. 5, pp. 623–628 (May 5, 1991).

Kohso, et al. "An Investigation of an infrared ray electronic endoscope with a laser diode light source", *Endoscopy*, vol. 22, pp. 217–220 (1990).

Kwong, K. F. et al. "400–Hz mechanical scanning optical delay line", *Optical Letters*, vol. 18, No. 7, pp. 558–560 (Apr. 1, 1993).

Mallery, J. et al. "Assessment of normal and atherosclerotic arterial wall thickness with an intravascular ultrasound imaging catheter", *American Heart Journal*, vol. 119, No. 6, pp. 1392–1400 (Jun. 1990).

Martinez, Oscar E. "3000 Times Grating Compressor with Positive Group Velocity Dispersion: Application to Fiber Compensation in 1.3–1.6 $\mu$m Region", *IEEE Journal of Quantum Electronics*, vol. QE–23, No. 1, pp. 59–64 (1987).

Morioka, T. "Nearly penalty–free, <4 ps supercontinuum WDM pulse generation for Tbit/s TDM–WDM networks", *Proc. Optical Fiber Comm*, paper PD21-1—PD21-4 (1995).).

Ng, K.H. et al. "Arterial Imaging with a new Forward–Viewing Intravascular Ultrasound Catheter, II Three–Dimensional Reconstruction and Display of Data", *Circulation*, vol. 89, No. 2, pp. 718–723 (Feb. 1994).

Pankratov, M.M. et al. "A Step–zoom probe for laser endophotocoagulation: Design", *Ophthalmic Surgery*, vol. 18, pp. 61–65 (1987).

Park, Heungsup, et al. "High resolution optical ranging system", *Applied Optics*, vol. 20, No. 14, pp. 2389–2394 (Jul. 15, 1981).

Piyaket, R. et al. "Programmable ultrashort optical pulse delay using an acousto–optic deflector"*Applied Optics*, vol. 34, No. 8, pp. 1445–1453 (Mar. 10, 1995).

Potkin, B. et al. "Coronary artery imaging with intrvascular high–frequency ultrasound", *Circulation*, vol. 81, No. 5, pp. 1575–1585 (May 1990).

Puliafito, C. "Imaging of macular diseases with optical coherence tomography", *Ophthalmology*, vol. 102, No. 2, pp. 217–229 (Feb. 1995).

Salathe, R. P., et al. "Coupled–mode propagation in multicore fibers characterized by optical low–coherence reflectometry", *Optics Letters*, vol. 21, No. 13, pp. 1006–1008 (Jul. 1, 1996).

Schaub, R. D. et al. "A New Fiber Optic Probe for Cellular Visualization", *ASAIO Journal*, pp. M665–M669 (1995).

Schmitt, J. et al. "Measurement of opticl properties of biological tissues by low–coherence reflectometry", *Applied Optics*, vol. 32, No. 30, pp. 6032–6042 (Oct. 20, 1993).

Scmitt, J. et al. "Optical–coherence tomography of a dense tissue: statistics of attenuation and backscattering", *Phys. Med. Biol.*, vol. 39, pp. 1705–1720 (1994).

Sergeev, A. et al. "In vivo optical coherence tomography of human skin microstructure", *SPIE Proc.*, vol. 328, p. 144–153 (1994).

Sergeev, et al. "High–spatial–resolution optical–coherence tomography of human skin and mucus membranes", *Conference on Lasers and Electro–Optics*, (May 1995).

Sorin, W. V., "Simultaneous Thickness and Group Index Measurement Using Optical Low–Coherence Reflectometry", *IEEE Photonics Technology Letters*, vol. 4, No. 1, pp. 105–107 (Jan. 1, 1992).

Swanson, E. A. et al. "High–speed optical coherence domain reflectometry", *Optics Letters*, vol. 17, No. 2, pp. 151–153 (Jan. 15, 1992).

Swanson, E. A., et al. "Optical Coherence Tomography: Principles, Instrumentation, and Applications", *ACOFT '96*, pp. 125–128 (Dec. 1–4, 1996).

Takada, et al., "New measurement system for fault location in optical waveguide devices based on an interferometric technique", *Applied Optics*, vol. 26, No. 9, pp. 1603–1605 (May, 1987).

Takada, et al., "Phase–noise and shot–noise limited operations of low coherence optical time domain reflectometry," *Appl. Phys. Lett.*, vol. 59, No. 20, pp. 2483–2485 (Nov., 1991).

Takada, K. et al. "Rayleigh backscattering measurement of single–mode fibers by low coherence optical time–domain reflectometer with 14 $\mu$m spatial resolution", *Appl. Phys. Letters*, vol. 59, No. 2, pp. 143–145 (Jul. 8, 1991).

Takada, K. et al. "Resolution control of low–coherence optical time–domain reflectometer between 14 and 290 $\mu$m", *IEEE Photonics Technology Letters*, vol. 3, No. 7, pp. 676, 678 (Jul. 1991).

Tateda, et al., "Water Penetration Sending Using Wavelength Tunable OTDR", *IEEE Photonics Technolgy Letters*, vol. 3, No. 1, pp. 1–3 (Jan. 1991).

Tearney, G. J., et al. "High–Speed phase–and–group–delay scanning with a grating–based phase control delay line", *Optical Letters*, vol. 22, No. 23, pp. 1811–1813 (Dec. 1, 1997).

Thurston, et al. "Analysis of picosecond pulse shape synthesis by spectral masking in a granting pulse compressor", *IEEE Journal of Quantum Electronics*, vol. QE–22, No. 5, pp. 682–695 (1986).

Tomkinson, Todd H., et al. "Ragid endoscopic relay systems: a comparative study", *Applied Optics*, vol. 35, No. 34, pp. 6674–6683 (Dec. 1, 1996).

Turnbull, D. H. et al. "A 40–100 MHz B–Scan Ultrasound Backscatter Microscope for Skin Imaging", *Ultrasound in Mid. And Biol.*, vol. 21, No. 1, pp. 79–88 (1995).

Wang, X. J. et al. "Characterization of fluid flow velocity by optical Doppler tomography", *Optics Letters*, vol. 20, No. 1, pp. 1337–1339 (Jun. 1, 1995).

Webb, R. H. "Optics for laser rasters", *Applied Optics*, vol. 23, No. 20, pp. 3680–3683 (1984).

Weiner, A. M. et al. "High–resolution femtosecond pulse shaping", *Journal of Optical Soc. Am. B.*, vol. 5, No. 8, pp. 1553–1572 (Aug. 1988).

Weiner, A.M. et al. "Programmable femtosecond pulse shaping by use of a multielement liquid–crystal phase modulator", *Optics Letters*, vol. 15, No. 6, pp. 326–328 (Mar. 15, 1990).

Yadlowsky, M. et al. "Multiple scattering in optical coherence microscopy", *Applied Optics*, vol. 34, No. 25, pp. 5699–5707 (Sep. 1, 1995).

Yasa, Z. A. et al. "A Rapid–scanning autocorrelation scheme for continuous monitoring of picosecond laser pulses", *Optics Communication*, vol. 36, No. 5, pp. 406–408 (Mar. 1, 1981).

Yock, P. et al. "Intravascular ultrasound guidance for catheter–based coronary interventions", *Journal of American College of Cardiology*, vol. 17, No. 6, pp. 39B–45B (May 1991).

Youngquist, et al., "Optical coherence–domain reflectometry: a new optical evaluation technique", *Optics Letters*, vol. 12, No. 3, pp. 158–160 (Mar., 1987).

Huang, et al., "Optical coherence tomography." Science 254: 1178–1181 (Nov. 1991).

Tearney, et al., "Scanning single mode catheter/endoscope for optical coherence tomography." Opt. Lett. 21: 543–545 (Apr. 1996).

Tearney, et al., "In vivo endoscopic optical biopsy with optical coherence tomography." Science 276: 2037–2039 (Jun. 1997).

Fujimoto, et al., "Optical biopsy and imaging using optical coherence tomography." Nature Medicine 1(9): 970–972 (Sep. 1995).

Brezinski, et al., "Optical Biopsy with optical coherence tomography: feasibility for surgical diagnostics." Journal of Surgical Research 71(1): 32–40 (Jul. 15, 1997).

Tearney, et al., "Optical biopsy in human urologic tissue using optical coherence tomography." The Journal of Urology 157(5): 1915–1919 (May 1997).

Boppart, et al., "High–resolution optical coherence tomography–guided laser ablation of surgical tissue." Journal of Surgical Research 82(2): 275–284 (Apr. 1999).

Boppart, et al., "Optical coherence tomography for neurosurgical imaging of human intracortical melanoma." Neurosurgery 43(4): 834–841 (Oct. 1998).

Herrmann, et al., "Two–and three–dimensional high–resolution imaging of the human oviduct with optical coherence tomography." Fertility and Sterility 70(1): 155–158 (Jul. 1998).

Brezinski, et al., "Assessing atherosclerotic plaque morphology: comparison of optical coherence tomography and high frequency intravascular ultrasound." Heart 77(5): 397–403 (May 1997).

Tearney, et al., "Optical biopsy in human pancreatobiliary tissue using optical coherence tomography." Digestive Diseases and Sciences 43(6): 1193–1199 (Jun. 1998).

Pitris, et al., "High resolution imaging of the upper respiratory tract with optical coherence tomography." Respiratory and Critical Care Medicine 157(5): 1640–1644 (May 1998).

Brezinski, et al., "Optical biopsy with optical coherence tomography" Advances in Optical Biopsy and Optical Mammography 838: 68–74 (1998).

Fujimoto, et al., "New technology for high–speed and high–resolution optical coherence tomography" Advances in Optical Biopsy and Optical Mammography 838: 95–107 (1998).

Tearney, et al., "Optical biopsy in human gastrointestinal tissue using optical coherence tomography." The American Journal of Gastroenterology 92(10): 1800–1804 (Oct. 1997).

Fujimoto, et al., "High resolution in vivo intra–arterial imaging with optical coherence tomography." Heart 82(2): 128–133 (Aug. 1999).

Boppart, et al., "Imaging developing neural morphology using optical coherence tomography" Journal of Neuroscience Methods 70(1): 65–72 (Dec. 1996).

Roper, et al., "In vivo detection of experimentally induced cortical dysgenesis in the adult rat neocortex using optical coherence tomography" Journal of Neuroscience Methods 80(1): 91–98 (Mar. 13, 1998).

Boppart, et al., "Intraoperative assessment of microsurgery with three–dimensional optical coherence tomography" Radiology 208(1): 81–86 (Jul. 1998).

Tearney, et al., "In vivo endoscopic optical biopsy with optical coherence tomography" Science 276: 2037–2039 (Jun. 27, 1997).

Herrmann, et al., "High resolution imaging of normal and osteoarthritic cartilage with optical coherence tomography" The Journal of Rheumatology 26(3): 627–635 (Mar. 1999).

Boppart, et al., "In vivo cellular optical coherence tomography imaging." Nature Medicine 4(7): 861–865 (Jul. 1998).

Pitris, et al., "High resolution imaging of gynecologic neoplasms using optical coherence tomography." Obstetrics & Gynecology 93(1): 135–139 (Jan. 1999).

Prince, et al., "Ball–Tipped Fibers for Laser Angioplasty with the Pulsed–Dye Laser." Journal of Quantum Electonics 26(12): 2297–2306 (Dec. 1990).

Valdya, et al., "Sculpted Optical Silica Fiber Tips for Use in Nd: YAG Contact Tip Laser Surgery: Part 1–Fabrication Techniques." Optical Engineering 31(7): 1404–1409 (Jul. 1992).

Hillerich, "Shape Analysis and Coupling Loss of Microlenses on Single–Mode Fiber Tips." Applied Optics 27(15): 3102–3106 (Aug. 1988).

\* cited by examiner

FUSION LENS

EPOXY LENS

GROUND/CORE BALL LENS

GROUND FIBER

GRADIENT-INDEX

ULTRA-SMALL OPTICAL PROBES, IMAGING OPTICS, AND METHODS FOR USING SAME

FIELD OF THE INVENTION

The present invention relates to the design and manufacture of ultra-small optical probes and methods of using the same. More particularly, the invention relates to the use of such probes in optical beam delivery and optical imaging techniques, such as Optical Coherence Tomography (OCT).

BACKGROUND OF THE INVENTION

Medical diagnostic techniques which rely on measuring the optical properties of a narrow, twisting lumen (e.g., small arteries and veins) or a small space (e.g., pulmonary airways) require ultra-small optical probes. These probes in turn require ultra-small imaging lenses and associated scanning and beam director elements. There exists a need in the art for ultra-small optical probes capable of being used in diagnostic medical devices such as guidewires, catheters, endoscopes, bronchoscopes, needles, and trocars.

The design of ultra-small optical probes for medical diagnosis has been limited by constraints on lens size. GRaded INdex (GRIN) lenses coupled to a fold mirror have been used in the design of a 1 mm catheter. However, although able to image the aperture of a single-mode fiber onto a vessel wall, the GRIN lens catheter known in the art cannot be scaled smaller than 1 mm since the diameter of the GRIN lens itself is on the order of 1 mm.

Techniques for making very small lenses have been described in the literature. However, these lens have small working distances and although suitable for coupling into laser diodes, do not offer the >1 mm working distance and the >1 mm depth-of-field required to image the internal structures of a human body in situ. Microlenses also have been described that can be used for high-power (short focal length) designs. These type of lenses typically use balls or micro-tapers that yield an overall lens diameter bigger than that of a single-mode fiber or have focal lengths that are too short for imaging the internal structures of a body in situ. Microlenses that are designed specifically for highly multi-mode fibers pose different theoretical considerations than do lenses which may be used with single-mode fibers and those described in the art reduce the size of the original beam rather than increasing it.

The present invention provides an optical fiber-lens system which can deliver light from a single-mode fiber, providing minimum back-reflection and minimum loss of light while delivering a nearly diffraction limited image in the focal plane of a sample. The optical fiber-lens system in combination with beam steering and scanning elements can be used as an optical probe to navigate small, tortuous paths within the human body.

SUMMARY OF THE INVENTION

The present invention provides an optical imaging probe comprising a single-mode optical fiber optically coupled to a lens which has substantially the same diameter as the optical fiber. In another embodiment of the invention, the optical imaging probe comprises a coreless fiber optically coupled to the single-mode fiber and the lens. In a further embodiment of the invention, the lens is in communication with a beam director.

The invention also provides an optical probe including a graded index lens. In another embodiment of the invention, the optical probe comprises a fold mirror. In one embodiment of the invention the fold mirror is spaced apart from the lens, while in another embodiment of the invention, the fold mirror is in physical contact with the lens.

The present invention also provides an optical probe having an optical fiber at least partially contained within a probe housing. In another embodiment, the probe housing is in the form of an insertional medical device, such as a guidewire, an endoscope, bronchoscope, a catheter, a needle, and a trocar.

The present invention also provides connectors to connect and disconnect the probe from an optical system. The connectors of the present invention have a first end for coupling to the probe housing of the optical probe and a second end for coupling to the optical system. In another embodiment of the invention, the probe housing is in the form of a guidewire and the first end of the connector has a diameter which is substantially the same size as the diameter of the guidewire.

In one embodiment of the invention, the optical probe comprises a pull back mechanism in communication with one of the housing and the optical fiber. Actuation of the pull back mechanism causes linear motion of at least one of the probe housing and optical fiber relative to the longitudinal axis of the optical fiber.

The present invention also provides an ultra-small lens for use with the optical probes. In one embodiment of the invention, the lens has a working distance of >1 mm. In a further embodiment of the invention, the depth of field of the lens is >1 mm. The invention also provides a method of manufacturing an ultra-small lens having these properties. In one embodiment, a graded index fiber is spliced to a coreless fiber. The coreless fiber is then precision cleaved at a predetermined position and spliced to a single-mode fiber. The graded index fiber is then precision cleaved at a proper distance to produce a lens with desired optical properties (e.g., a large working distance and depth of field).

The invention also relates to a method of measuring the optical properties of a test sample in situ. An optical probe is positioned in proximity to the test sample, the optical probe comprising a single-mode optical fiber optically coupled to a lens which is substantially the same diameter as the optical fiber. An optical beam is then transmitted from the optical probe to a sample in situ and light transmitted from the sample is detected.

BRIEF DESCRIPTION OF THE DRAWINGS

The foregoing and other objects, features, and advantages of the present invention, as well as the invention itself, will be more fully understood from the following descriptions of preferred embodiments, when read together with the accompanying drawings, in which:

FIG. 9A shows a connector in the form of a ferule. FIG. 9B shows a quick disconnect unit in which the ferule and optical probe are seated within a quick disconnect housing. FIG. 9C shows an enlarged view of a quick disconnect unit where the unit includes a split-sleeve.

DETAILED DESCRIPTION OF THE INVENTION

The present invention discloses the design of an ultra-small optical imaging probe that can perform circumferential imaging of a sample. The invention also provides methods of manufacturing the micro-optical elements (e.g., microlenses and beam directors) that form the distal imaging optics of such a probe. The present invention provides probes with lenses less than ~300 um in diameter which simultaneously have a working distance that can extend up to several millimeters.

Micro-Optical Elements

For many imaging systems (e.g., OCT imaging systems), light is emitted from an single-mode optical fiber and focused on a sample using a lens. Retro-reflected light is then coupled back through the lens into the fiber. In contrast to optical systems which rely on multimode optical fibers where the beam waist location and the classical image location are nearly coincident, in optical systems including single-mode optical fibers which emit a nearly Gaussian beam, the waist location and the classical image location can be significantly different. This difference must be taken into account when designing lens to be coupled with single mode optical fibers in order to attain the desired image location and depth of field.

Figure 1:
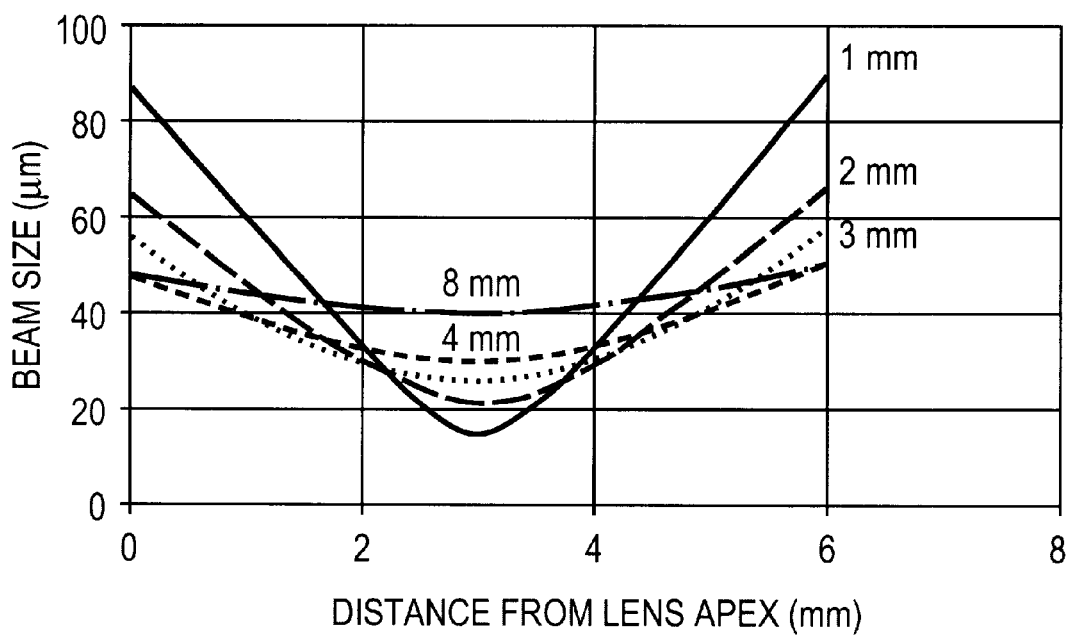
FIG. 1 shows the relationship between resolution and depth of field for a Gaussian beam.

In OCT and other imaging or light delivery/collection applications, the best optical performance is obtained when light impinges on a sample that is located within the depth of field of the lens. This ensures that any light back-reflected from a sample will be efficiently directed back through the single mode fiber. Light back-reflected farther and farther outside the working distance of the lens is received less and less efficiently by the single-mode optical fiber and hence is less detectable by the imaging system. Increasing the depth of field of the lens allows an optical probe to image farther into a vessel or space into which the probe is inserted. FIG. 1 shows the relationship between the spot size of a light beam transmitted through a single-mode optical fiber and the depth of field that can be generated assuming a Gaussian beam and a working distance of 3 mm. The trade-off between depth of field (e.g., 1, 2, 3, 4, and 8 mm) and corresponding beam spot size (14, 20, 25, 29, and 41 $\mu$m) for a wavelength of 1.33 $\mu$m is clearly apparent. The depth of field is inversely related to the square of the beam spot size; thus, decreasing the beam spot size concurrently decreases the depth of field. Thus, the challenge in making small optical systems has been to achieve a both a large working distance and a large depth of field and still maintain a small optical probe diameter and small beam spot size. Optical systems having small beam spot sizes and large working distance have previously only been obtained at the expense of increasing lens size, and therefore ultimately at the expense of increasing the size of the optical probe.

In small optical imaging probes known in the art, a single-mode fiber 125 $\mu$m in diameter is typically glued to a commercial 700 $\mu$m Graded Index (GRIN) lens using ultraviolet-cured optical adhesive ("UV glue"). The GRIN lens in turn is UV-glued to a 700 $\mu$m fold mirror, such as a prism, forming an optical chain comprising the single-mode optical fiber, the GRIN lens, and the fold mirror. The proximal end of the GRIN lens is fixedly held within a rotable torque cable. The entire assembly (i.e., optical chain and torque cable) is contained within a sheathing. The sheathing is typically transparent to the wavelength of light contained with the single-mode fiber or includes a transparent window near the fold mirror.

While this type of imaging optical probe can achieve the resolution, depth of field, and beam spot sizes illustrated in FIG. 1, it does so at the expense of size. The entire assembly of such a probe is approximately 1 mm in diameter even though the optical fiber within the device is only 125 $\mu$m in diameter and the largest beam size required to obtain a suitable working distance for imaging is less than 100 $\mu$m (see FIG. 1). This large diameter limits the use of probes known in the art to imaging openings significantly greater than 1 mm. In the human body (and in other non-medical applications) there is a pressing need to miniaturize the diameter of the imaging probe so that smaller vessels can be navigated. For example, guidewire applications require that the entire outside diameter of the guidewire may be only 350 $\mu$m in order to fit in most catheter devices. However, typical optical probes have difficulty in being scaled down to the diameter required for a guidewire because the lenses of such probes typically have a diameter on the order of 1 mm.

Most small optical probes known in the art also suffer from large back-reflections of light as it is difficult to match the indices of refraction of the various optical elements of the probe (e.g., lens and fold mirror/prism) to each other. These back-reflections can significantly impact the quality of images obtained, particularly in OCT applications where large back-reflections lead to an effect known in the art as blindness—whereby a large reflection tends to saturate the front-end electronics of the detecting component of the imaging system, rendering small reflections generated by the actual sample undetectable.

The present invention provides methods to design miniature lenses 2 (~250 $\mu$m in diameter) that can achieve optical parameters similar to those shown in FIG. 1. In different embodiments of the invention, microlens 2 are provided which include the following optical properties:

A lens 2 diameter of less than about 300 $\mu$m (preferably less than about 150 $\mu$m);

A working distance >1 mm;

A depth of field >1 mm;

A spot size of <100 μm;

Ability to work within a medium with an index of refraction >1 (e.g., within a saline or blood-filled environment) without destroying the image quality;

Ability to rotate or perform circumferential scanning within a 400 μm diameter housing;

Ability to achieve >20% coupling efficiency from a fold mirror 3 located at the beam waist location of the lens 2; (Coupling efficiency is defined here as the amount of light energy recoupled or redirected by the lens 2 system back into the fiber 1.)

Minimal back-reflections; and

Ability to use as part of an ultra-small optical probe which forms a guidewire apparatus.

Figure 2A:
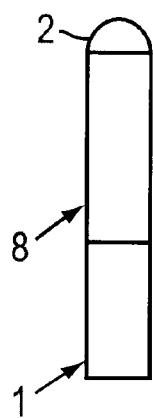
FIGS. 2A–E show optical fiber-lens systems having different types of microlenses according to embodiments of the invention.
Figure 2B:
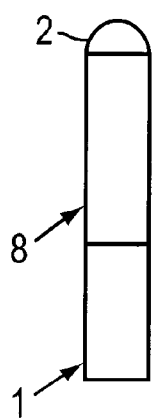
Figure 2C:
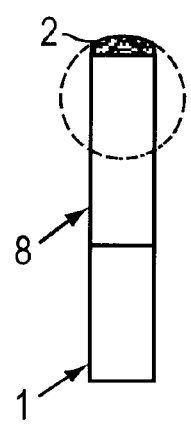
Figure 2D:
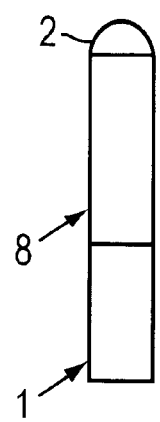
Figure 2E:
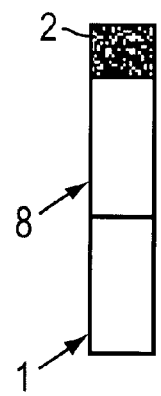

FIGS. 2A–E show microlenses 2 that can be manufactured efficiently according to the methods disclosed herein while achieving the parameters listed above. There are two basic types of lenses 2: (1) lenses 2 that use a radiused end (FIGS. 2A–D) and (2) lens 2 that use a longitudinal or radially varying index (e.g., GRIN lenses) (FIG. 2E). Combinations of both types of lens may also be used. In a preferred embodiment of the invention, all of the lenses 2 are optically coupled to a single-mode fiber 1. A single-mode optical fiber 1 typically consists of an 80 μm or 125 μm cladding and a 4 to 10 μm core as is known in the art.

In order to achieve the working distances and optical parameters shown in FIG. 1, the lens 2 typically cannot be directly affixed to the single-mode fiber 1 because it is necessary that an optical beam transmitted through the optical fiber 1 first expand to the required beam diameter prior to being focused by the lens 2. In one embodiment of the invention, the space between the lens 2 and the single-mode fiber 1 is filled by a coreless fiber 8. The length of the coreless fiber 8 is calculated by selecting optical properties the user desires in the optical probe. For example, to image (in air) with a 4 mm depth of field, a 29 μm spot size, and a 3 mm working distance would require ~810 μm of coreless fiber 8 followed by a lens 2 with a spherical surface having a radius of curvature of ~225 μm.

Figure 3:
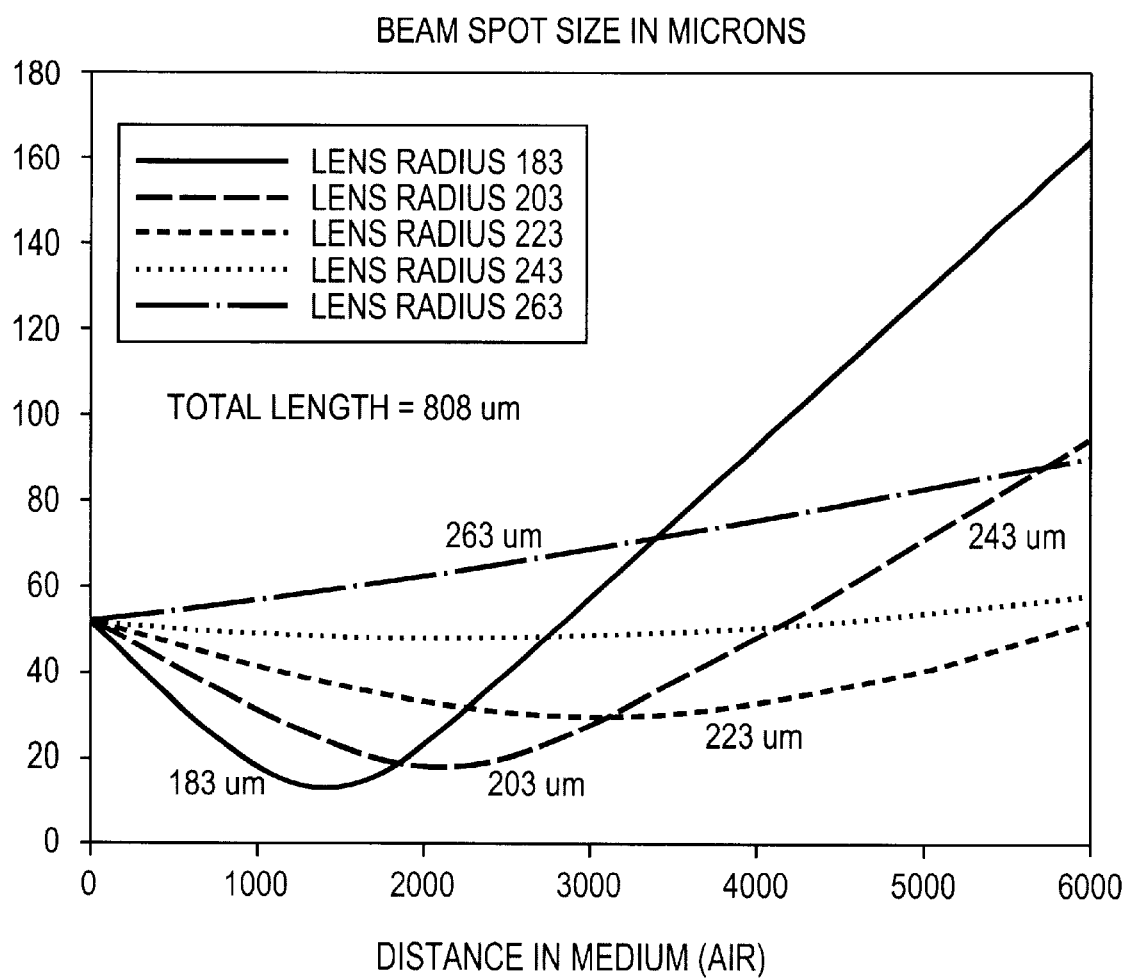
FIG. 3 is a graph showing the relationship between beam waist size and lens radius of curvature.

FIG. 3 shows the relationship between the beam spot size and the lens 2 radius of curvature for a coreless fiber 8 having a length of ~810 μm and lenses 2 with varying radii of curvature. The design of the lens 2 system can be accomplished with knowledge of Gaussian beam propagation which is well detailed in many standard textbooks. The equations as applied to the newly disclosed microlenses 2 are outlined below.

Figure 4:
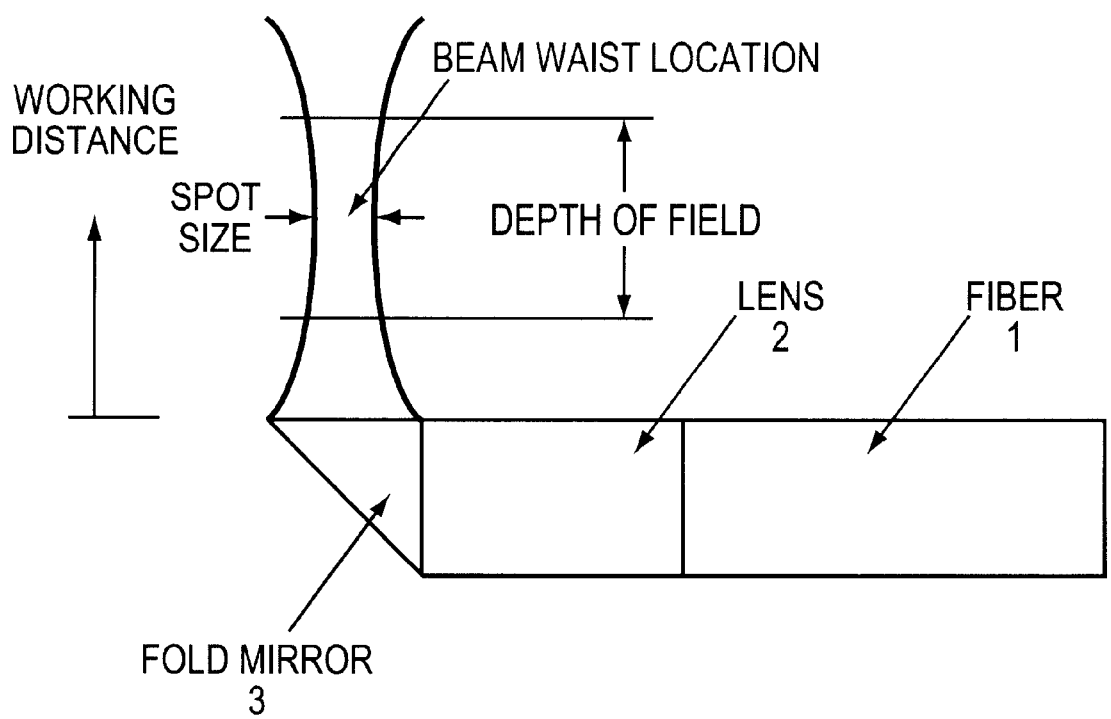
FIG. 4 shows an optical probe according to one embodiment of the invention including a single-mode optical fiber and a lens which is substantially the same diameter as the optical fiber.

First, single-mode Gaussian beams expand from their minimum (the "waist") according to the well-known relationship:

$$\omega(z) = \omega_0 \sqrt{1 + \left(\frac{z}{z_0}\right)^2} \quad (1)$$

where $\omega(z)$ is the beam radius at location z, $\omega_0$ is the beam waist which occurs by definition at z=0, and $z_0$ is the Rayleigh range and is the distance at which the peak intensity falls to ½ of its value as measured at the beam waist. The Rayleigh range is given by $\eta\pi\omega_0^2/\lambda$, where $\lambda$ is the wavelength of the light in a vacuum, and $\eta$ is the index-of-refraction of the medium. The Rayleigh range thus dictates the depth of field of the lens 2, which is typically defined as twice $z_0$ and is often called the confocal parameter. As shown in FIGS. 1 and 4, the distance from the waist location of the imaged beam back to the lens 2 surface is defined here as the working distance of the lens 2.

Second, the radius of curvature, R(z), of a Gaussian beam follows another well-known relationship:

$$R(z) = z_0\left(\frac{z}{z_0} + \frac{z_0}{z}\right) \quad (2)$$

Equation 2 demonstrates that a Gaussian beam has an infinite radius of curvature (i.e., flat phase front) at the beam waist, and that at distances which are large compared to the Rayleigh range, a Gaussian beam will propagate much like a spherical wave centered at z=0 and can be treated in this regime with classical (geometrical) optics. In the case at hand, however, the desired working distances (z) and depth of fields ($z_0$) are comparable and classical optics cannot be used effectively. To solve this problem, a desired working distance and depth of field for lens 2 are chosen. These parameters determine the required beam waist size to be created by the lens 2. The required waist size and desired location of the beam waist in space in turn determine the required beam size, as well as the phase front radius of curvature (of the outgoing beam) at the lens 2 surface. Thus, the coreless fiber 8 between the single-mode fiber 1 and the lens 2 must allow the beam to expand from the exit of the single-mode fiber 1 to match the beam size required at the surface of the lens 2. The lens 2 must also bend the phase front of the incoming beam from the sample to match that of the outgoing beam transmitted through the single-mode fiber 1. Hence, the coreless fiber 8 and the lens 2 radius of curvature are uniquely determined given two input requirements (and given the single-mode fiber geometry and wavelength)—working distance and depth of field.

Using Equations 1 and 2 above, and assuming that the radial distances are small when compared to the longitudinal distances (the well-known paraxial approximation, a valid assumption for long-working-distance lens 2 designs as described herein), a simple relationship can be derived for the required radius of curvature:

$$\frac{1}{R_{lens}} = \frac{n_0}{n_1 - n_0}\left(\frac{1}{R_f} + \frac{n_1}{n_0 R_i}\right) \quad (3)$$

where $R_{lens}$ is the radius of curvature of the lens 2 surface, $n_1$ is the index of the coreless fiber 8, $n_0$ is the index of the medium (nominally air or saline) in which the new waist is formed, and $R_i$ and $R_f$ are the curvatures of incoming and outgoing Gaussian beams, respectively. The required length of the coreless fiber 8 can be easily calculated using Equation 1. Thus, using the calculations described above (for a fixed lens 2 length and which is parameterized by the length of the coreless fiber 8), the appropriate radius of curvature of a lens 2 required to achieve the properties of large working distance and depth of field and small beam spot size may be determined.

FIG. 3 is a graph showing the relationship between the beam spot size and the location of the beam waist for lenses 2 having a variety of curvatures calculated in this manner. It can be seen that a lenses 2 with a steep curvature (small radius of curvature) produces the smallest beam waist at the shortest distance as expected. Note that these equations are approximate and that more detailed and precise analysis can be preformed using commercially available physical optics design packages. These include, but are not limited to, CODE V (Optical Research Associates, Pasadena, Calif.), OSLO (Sinclair Optics, Inc., Fairport, N.Y.) and GLAD (Fraunhofer IAO, Stuttgart, Germany) commercial optical beam and design packages.

Figure 5:
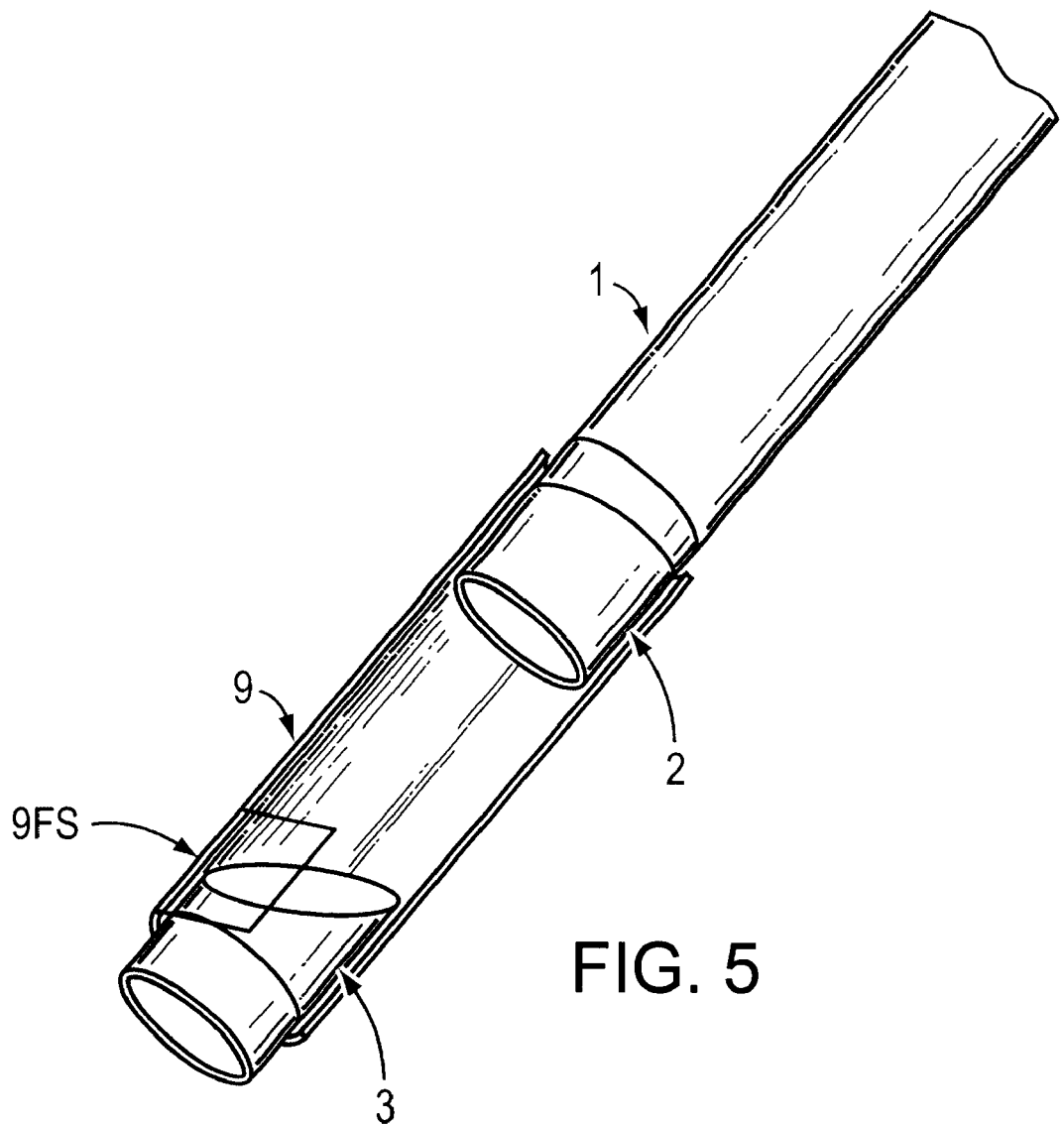
FIG. 5 shows an optical probe according to one embodiment of the invention including a fold mirror spaced apart from a microlens.

FIG. 4 is a schematic showing the properties of an optical beam obtained from an optical probe which includes the microlens 2 discussed above. In one embodiment, a single-mode fiber 1 is spliced or otherwise secured to the lens 2. The lens 2 is approximately the same diameter as the single-mode optical fiber 1. The optical fiber 1 may include a variety of thin coatings to ruggedize it which can be commercially purchased from Corning® (Corning Incorporated, Corning, N.Y.), Spectran® (Spectran, Sturbridge, Mass.), and other commercial fiber optic companies. A 90 degree (or other suitable angle) fold mirror 3 is affixed to the lens 2 also using splicing or glue. The fold mirror 3 is coated with a high reflectance material or operates in total internal reflection. In one embodiment, the fold mirror 3 is made of metal and is located separately from the lens (e.g., as shown in FIG. 5). In another embodiment of the invention, the fold mirror 3 is made by polishing another section of coreless fiber on a 45 degree (or other angle for forward or backward scanning) which is then metal- or dielectric-coated. In a further embodiment of the invention, the fold mirror 3 has a dichroic coating to allow one wavelength to reflect and one wavelength to simultaneously transmit through the mirror 3.

It should be noted that although fold mirrors 3 are described in examples throughout the specification, any type of optical element which can steer a light beam and serve as a beam director 3 is encompassed within the scope of the invention. Thus, the terms "beam director" 3 and "fold mirror" 3 are used interchangeably herein.

As can be seen in FIG. 4, the design of the microlenses 2 of the present invention minimizes the beam spot size at the working distance of the lens 2 and creates a nearly flat phase front of the beam at this location, i.e., forming a beam waist at a spot located at the working distance of the lens. The equations disclosed above predict a working distance (defined here as the beam waist distance as measured from the apex of the lens 2) of 3 mm for a lens 810 $\mu$m in length, with a radius of 225 $\mu$m, an operating wavelength of 1.32 $\mu$m, and a material index of refraction of 1.45.

Referring again to FIGS. 2A–E, in one embodiment of the invention, coreless fiber 8 region is directly attached to a single-mode fiber 1. As discussed above, in the coreless fiber 8 region an optical beam transmitted through the single-mode optical fiber 1 can gracefully expand to the required diameter of the lens 2 prior to focusing by the lens 2. The coreless fiber 8 can have the same diameter as the single-mode fiber 1 cladding and can be directly fusion-spliced using standard fusion splicer equipment, such as an Ericcson Fusion Splicer (Amherst Instruments, Amherst Fiber Optics, Brentwood, Tenn.), ensuring low loss, solid adhesion, and preservation of the single-mode Gaussian beam characteristics. Preferably, the coreless fiber 8 is index-matched to the single-mode fiber 1 to ensure minimum back-reflection and loss.

The optic fiber 1-lens 2 assemblies in FIG. 2A–D use lenses 2 with curved surfaces. The length of the coreless fiber 8 region and radius of curvature of the lenses 2 are chosen to obtain the required beam parameters (i.e., beam spot size, depth of field, and working distance) such as those shown in FIG. 1 and described previously. A number of methods of manufacturing the required lenses 2 are encompassed within the scope of the invention. These include using heat from a fusion splicer to melt the end of a coreless fiber 8 where surface tension will create a nearly circularly symmetrical lens 2 (FIG. 2A). In this embodiment, the fusion time and fusion current (heat) of the fusion splicer are adjusted and the manufacturer manipulates the end of the coreless fiber 8 relative to the fusion arc produced by the fusion splicer. Typically, to make large radius of curvature lenses 2 it is beneficial to run a relatively cool fusion arc (8–10 mA on an Ericcsson fusion splicer, for example) for a long time (1–30 seconds) or to make a long series of very short, high temperature fusion spikes. In a further embodiment of the invention, it is possible to test the radius of curvature of the lens 2 in real-time by monitoring the output using a high magnification microscope between fusion treatments or by removing the lens 2 and placing it into a beam profiling device such as those available from Beamscan (Photon, Inc., Santa Clara, Calif.). This way the recipe for the particular fusion splicer (or other heat treatment method) can be optimized for the particular lens parameters desired by an iterative method.

In a further embodiment of the invention (FIG. 2B), a small drop of UV or other suitable glue can be placed using a micropipette and cured on the end of the coreless fiber 8. When assembling a lens with the UV glue technique, it is preferable to select a volume of glue and a type of glue with the proper surface tension and viscosity so that upon placing the glue on the end of the coreless fiber 8, surface tension and viscosity cause the glue to "ball-up" with the desired surface profile and radius. With a large volume of glue approximately equal to a hemisphere on the end of the coreless fiber 8, the radius of curvature will approximately equal the radius of the coreless fiber 8 (and therefore, also the radius of the single-mode fiber 1). For smaller glue volumes, the radius can be increased to approximately 5 to 10 times the radius of the coreless fiber 8.

The radius of curvature of the lens 2 can further be slightly modified by locating the coreless fiber 8 vertically, with gravity pulling the glue down, to flatten the radius of curvature. In another embodiment, the coreless fiber 8 is held upside down to slightly increase the radius of curvature. The amount of glue can be controlled using a micropipette or by sequentially transferring a large ball of glue from the end of one fiber to a coreless fiber 8 without any glue. The volume of the glue will tend to decrease by a factor of two for each transference. Other methods known by those skilled in the art can be used to setting the proper volume of glue to be placed on the end of the coreless fiber 8 and cured.

Commercially available ball lenses (with appropriate shaping) 2 can also be shaped to a diameter nearly equal to the single-mode optical fiber 1 diameter and secured to the end of the coreless fiber 8 using UV or another suitable glue as shown in FIG. 2C. This can be accomplished by polishing the ball lenses 2 to form small, thin hemispheres or by coring the ball lenses 2 to form rod lenses 2.

Finally, the end of the coreless fiber 8 distal to the single-mode fiber 1 can be mechanically ground using grinding and polishing techniques known in the art. In this embodiment, the end of the coreless fiber 8 forms the lens 2 as shown in FIG. 2D. Ideally, the coreless fiber 8 is made to have the same index of refraction as the lens 2 to minimize loss and back-reflections of the optical beam transmitted from the single-mode fiber 1. In this embodiment, the coreless fiber 8 and lens 2 are one integral unit.

In a further embodiment of the invention, radiused lenses 2 may be manufactured using reflow technology whereby a material (e.g., polymethyl methacrylate (PMMA)) is deposited on the end of the coreless fiber 8 and heated so that material reflows to form a nearly circularly symmetrical lens 2.

In another embodiment of the invention, the radiused microlenses 2 of FIGS. 2A–D, as well as the flat lens 2 shown in FIG. 2E, can be affixed to an external fold mirror 3, as shown in FIG. 5. The fold mirror 3 is metered (or registered) with respect to a lens 2 using a clear plastic or glass metering tubing or cover 9 of optical quality. Other types of metering are possible and encompassed within the scope of the invention. In one embodiment, a metal or non-optically transparent media is used and a small hole is cut or placed at an appropriate location with respect to the fold mirror 3. If a small hole is cut or placed at the appropriate location above the fold mirror 3 to permit an optical beam to pass through the hole, the diameter of the metering tubing 9 (and thus the total outer diameter of the lens 2/beam director 3 assembly) can easily be made to less than 250 µm.

It is important to minimize the cylindrical lens effects of the metering tubing 9 shown in FIG. 4. This cylindrical lens effect may be compounded when the ultra-small optical probe is placed in saline or in another environment such as blood. In this case, the cylindrical surface of the tubing 9 (combined with the index of the sample medium) may act as a cylindrical lens more powerful than microlens 2 and can become a major detriment to the imaging quality of the system. However, the present invention provides methods to circumvent this effect. In one embodiment, a plastic metering tubing 9 is used and a flat spot 9fs is created in the tubing 9 by heat-treating the tubing 9. Alternatively, it is possible to index-match the tubing 9 material to the sample medium. For example, if the probe is to be placed in saline or blood, both having an index of refraction of ~1.3, then the tubing 9 is made with a similar index of refraction, i.e., ~1.3. In a further embodiment of the invention, an optical transmitter is placed between the lens 2 and the fold mirror 3 which also has a similar index of refraction of ~1.3. When index-matching the lens 2, it is important to use a lens 2 that has a radiused end (FIGS. 2A–3D) to take into account differences between the refractive indices of the sample medium, the optical transmitter and the lens 2. Lenses 2 that have an aspheric surface are also within the scope of the invention. Aspheric lenses are most easily made using the reflow technology described above. Finally, another method of avoiding the cylindrical lens effect of the metering tubing 9 is to simply avoid using a metering tubing 9 which is cylindrical. In one embodiment of the invention, the metering tubing 9 is made from commercially available square tubing (plastic or glass). Square tubing can also be made in several ways, such as by heat shrinking over a square metal wire or glass fiber, by extruding the tubing square, or by blow molding the tubing.

For many applications, the last lens 2 shown in FIG. 2E is the preferred embodiment. This lens 2 can be made in several ways. In one embodiment of the invention, a lens 2 having a graded index of refraction is used. In this embodiment of the invention, radial (or longitudinal) variation in the index of refraction of the GRIN lens 2 causes the phase front of the light beam transmitted through the optical fiber 1 yo be bent in a way which is analogous to the phase bending obtained from a conventional curved-surface lens. Materials for such lens 2 are commercially available and are known in the art as GRIN materials. Ideally, the gradient profile of the lens 2 is selected to be cylindrically symmetric and to decrease with a quadratic (or nearly quadratic) dependence on the radial distance from the center of the lens 2 as described in the following equation:

$$n(r) = n_c(1 - (A/2)(r/a)^\alpha) \quad (4)$$

where n(r) is the index of refraction, $n_c$ is the index of refraction in the center of a selected fiber to which the GRIN lens is attached (the GRIN lens may be either a single-mode, coreless, or a type of multimode fiber), r is the radius, A is the index gradient coefficient, a is the core radius, and α is the index power, which for a quadratic profile has a value of ~2. To minimize total back reflection, the center index of the lens 2 would be made to match the single-mode fiber 1 core (or the coreless fiber 8) index. The equivalency of a GRIN lens 2 (α=2) to a conventional lens is approximated by the following equation:

$$\frac{n_1 - n_0}{R_l} = n_c \frac{A}{a^2} l_{grin} \quad (5)$$

where $l_{grin}$ is the length of the GRIN lens 2 required, and the other parameters are as given earlier.

It is possible to use standard or custom multimode optical fiber that has a nearly quadratic index profile to make these lenses 2. Typical values of α for lenses used in telecommunications applications have a value of 1.8–1.9. Values of α close the ideal of 2.0 have been demonstrated both experimentally and theoretically to achieve acceptable Gaussian beam imaging. Thus, using commercial multimode fiber as a lens 2 material is a viable option. It is well-known that once a fiber "pre-form" (typically a large cylinder weighing several kilograms) is created with a given index gradient, it is possible to "pull" the final fiber to almost any desired diameter and thus achieve a variety of lens power and length combinations as can be seen from Equation (5). Further, it is even possible to post-machine a lens preform to change the core-to-cladding ratio and thus achieve an even wider variety of possible GRIN lenses 2. Thus, there are a variety of techniques available which allow one to take standard telecommunications fiber pre-forms and to modify the final fiber to suit the current purpose.

In one embodiment of the invention, multimode lenses with graded index profiles are made by using an industry-standard SMF-28 single-mode fiber 1 as the primary light guide, attaching ~750 µm of coreless fiber 8 (for beam expansion), and then attaching ~100 µm of multimode fiber (α of 1.8, A of 0.038) to the coreless fiber 8. The multimode fiber then serves as the lens 2. The multimode fiber is precision cleaved at a predetermined position based on calculations described above to achieve a desired working distance and depth of field.

A graded index lens 2 made by the disclosed method can achieve a beam waist radius size of ~30 µm and a beam waist location of nearly 2 mm from the fiber tip of the optical probe (i.e., the distal end of the GRIN lens). The lens 2 has a very high Gaussian beam quality, where quality is defined as the deviation of the measured beam intensity profile from the ideal Gaussian profile. Beam quality is important, both for image quality considerations, and for light recoupling efficiency considerations. The multimode fiber forming the lens 2 can be similar to standard Spectran® 62.5/125 multimode fiber. However, it is also desirable to have a larger ratio of core to cladding. In one embodiment of the invention, fiber similar to 62.5/125 multimode fiber is ordered from commercial sources (e.g., Lucent® Technologies, Murray Hill, N.J.; SpecTran Specialty Optics, Avon, Conn.) and the fiber is drawn to the size of 105/125 multimode fiber. The graded index profile is then simply scaled down from 62.5 to 105 µm in diameter.

The coreless fiber 8 can be eliminated if the gradient coefficient is reduced enough to allow the beam to expand to its required diameter while traversing the GRIN lens 2. Commercially available multimode fiber as well as GRIN lens known in the art have a the gradient coefficient that is too strong (i.e., an A coefficient that is too large) for the designs presented here. However, the present invention provides methods to achieve customized gradients. To calculate the required GRIN gradient profile for a lens 2, the standard ABCD matrix formalism for treating Gaussian beam propagation in the paraxial approximation can be used. The ABCD matrix describing the propagation from a single-mode fiber 1 through a GRIN material and into the medium interface is given by:

$$\begin{bmatrix} A & B \\ C & D \end{bmatrix} = \begin{bmatrix} \cos(l_{grin}A') & \dfrac{n_{sinf}}{n_c A'}\sin(l_{grin}A') \\ -\dfrac{n_c A}{n_0}\sin(l_{grin}A') & \dfrac{n_{sinf}}{n_0}\cos(l_{grin}A') \end{bmatrix} \quad (6)$$

where A' is $(\sqrt{A})/a$, and $n_{smf}$ is the index of the single-mode fiber 1. The ABCD law for the transformation of Gaussian beams can be used to solve for the A' parameter given the other material parameters and, as before, the desired depth of field and working distance. With some algebraic manipulation, two equations can be derived:

$$\dfrac{1}{\omega_f^2} - \dfrac{1}{\omega_i^2}\left(\cos^2(l_{grin}A') + \left(\dfrac{n_c A' \pi \omega_i^2}{\lambda}\right)^2 \sin^2(l_{grin}A')\right) \quad (7)$$

$$\dfrac{1}{W_D} = \left(\dfrac{n_{sinf}}{n_0}\right)^2 \dfrac{1}{\sin(l_{grin}A')\cos(l_{grin}A')\left(\left(\dfrac{\pi\omega_i^2}{\lambda_{sinf}}\right)^2 \dfrac{n_c A'}{n_0} - \dfrac{n_{sinf}^2}{n_c n_0 A'}\right)} + \dfrac{n_c A' \sin(l_{grin}A')}{n_0 \cos(l_{grin}A')} \quad (8)$$

where $w_f$ is the final (imaged) beam waist radius, $w_i$ is the initial beam waist radius at the exit of the single-mode fiber 1, $\lambda$ is the free-space wavelength, $\lambda_{smf}$ is the wavelength inside the single-mode fiber 1, and $W_D$ is the working distance (e.g., location of the imaged waist). For example, given a desired length of field of 4 mm and a working distance of 3 mm, with $\lambda$ equal to 1.32 μm, Equations (7) and (8) can be iteratively solved to yield A'=1.2074 mm$^{-1}$ and $l_{grin}$=1.41 mm, starting wit standard Corning® SMF-28 fiber and imaging in air. Again these formulae are approximations to the exact solution and is possible to use numerical optical design software, such as CODE V (Optical Research Associates, Pasadena, Calif., OSLO (Sinclair Optics., Fairport N.Y.) and GLAD (Escandido, Calif. U.S.A.), to get more precise lens 2 designs, although these models are not as instructive as the equations presented above.

Elimination of the coreless fiber 8 region results in a significant savings in the complexity of the lens 2 system as the number of fusion splices and precision cuts is reduced two-fold. Another advantage of customizing the GRIN material is that the effects of the fold mirror 3 (i.e., the impact of additional optical length and material indices) can be incorporated into the higher algebraic equations discussed above and/or into physical models so that the A coefficient can be optimized for the complete system including beam director/fold mirror 3.

One significant advantage of the lens 2 system in FIG. 2E over the radiused lenses 2 shown in FIGS. 2A–3D is that an optical probe comprising this type of lens 2 can be immersed in saline or in another environment (e.g., blood or tissue) with an refractive index not equal to 1 and can still be used to image. The reason for this is that while conventional lenses perform all of the bending of the phase front of the light beam from the optical fiber 1 directly at the interface between the sample medium and lens medium, GRIN materials perform the phase bending within the GRIN medium itself. Moreover, as shown in FIG. 6, an integral fold mirror 3 can be directly attached to the lens 2.

In one embodiment of the invention, the fold mirror 3 is be made by purchasing "D-core" fiber (i.e., a fiber formed in the shape of the letter "D") or square fiber (such as obtained from Lucent Technologies, Murray Hill, N.J., SpecTran Specialty Optics, Avon, Conn.) or by polishing a fiber to have a flat facet along its length to create the desired D-shape. The D-fiber is then spliced onto a GRIN/multimode fiber lens 2 and the end is polished on a 45 degree angle (or other suitable angle for forward or reverse imaging) to reflect the outgoing beam from the single-mode optical fiber 1 through the flat of the D (thus avoiding parasitic cylindrical lens effects). The mirror 3 can then be either metal -or dielectric-coated or, as mentioned above, can be coated with a dichroic beam splitter to allow simultaneous forward and side imaging via different wavelengths. Alternatively, if the angle of the fold mirror 3 is greater or less than the angle for total internal reflection of the fold mirror 3, as given by Snell's law (~45 degrees in silica/air interface), then it is not necessary to coat the mirror 3.

Figure 6:
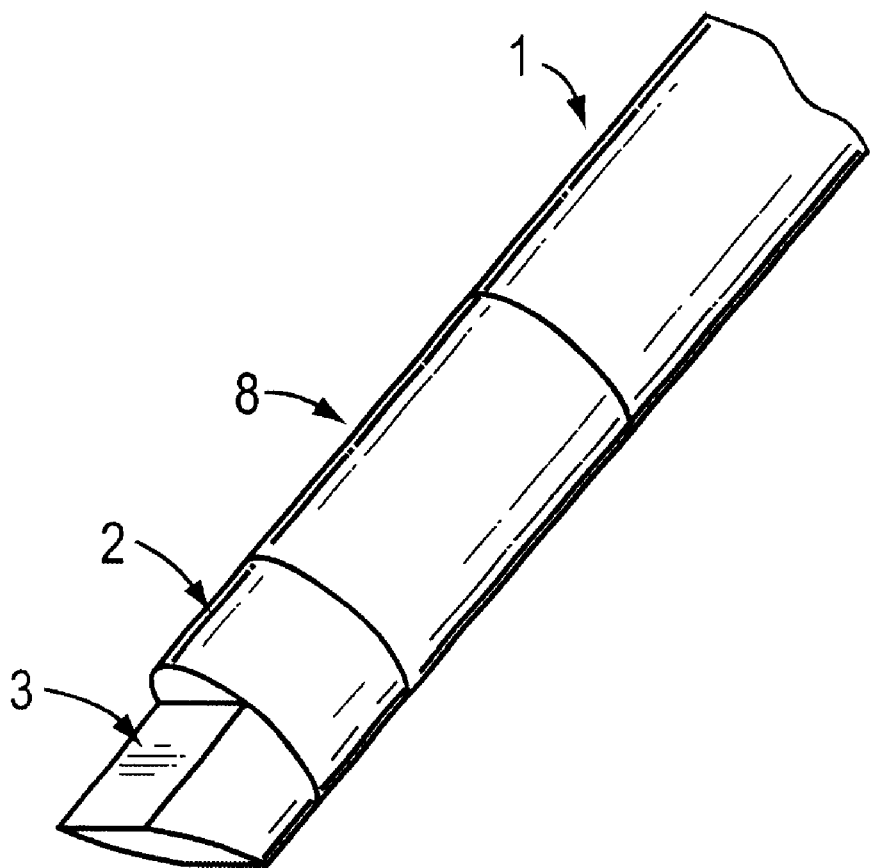
FIG. 6 shows an optical probe according to one embodiment of the invention including a fold mirror in physical contact with a microlens.

The total diameter of the optical lens 2/fold mirror 3 in FIG. 6 can easily be made less than 250 μm while obtaining the desired beam parameters (e.g., as shown in FIG. 1). Further, the lens 2 can be made using standard fusion splicing and polishing techniques, and thus can be low cost, with minimal back-reflections and maximal performance. It is also possible to make the integral fold mirror 3 of FIG. 6 by first fusion splicing a short section of coreless fiber 8 to the GRIN lens 2, then polishing the edge of fold mirror 3 flat or on a slight angle. In a further embodiment of the invention, it is possible to make a section of a coreless fiber 8 square-shaped or D-shaped during the fiber draw to form the fold mirror 3. The fold mirror 3 can also be made using polishing, cleaving, or sawing techniques.

Figure 7:
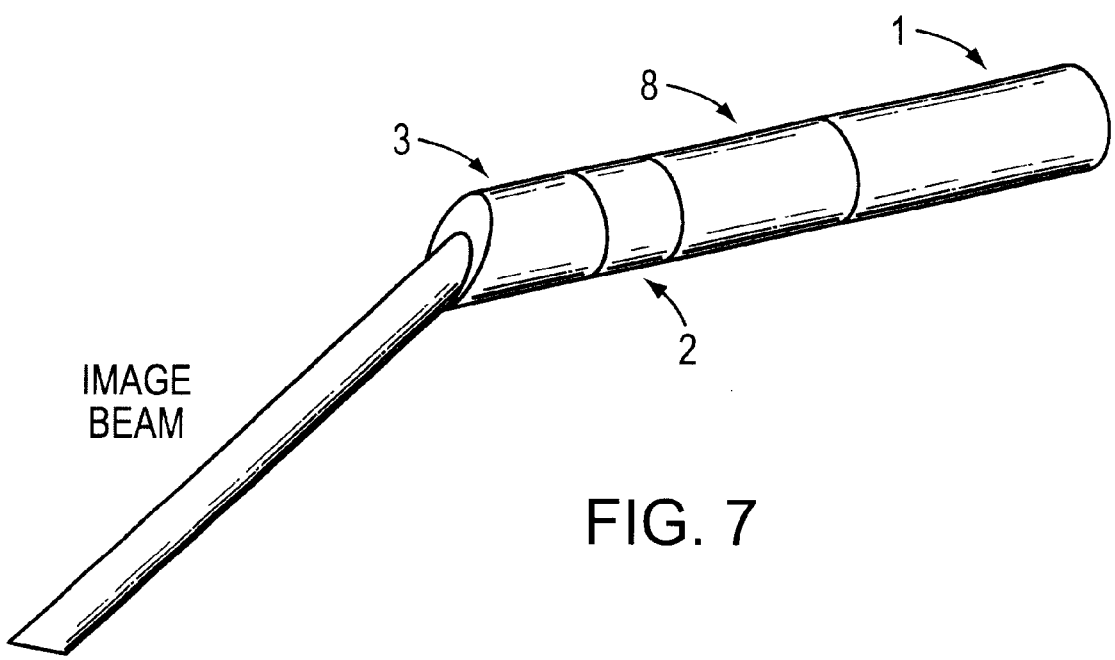
FIG. 7 shows an optical probe according to one embodiment of the invention directing a beam for forward imaging of a sample.

In another embodiment of the invention shown in FIG. 7, a section of a coreless fiber is optically coupled to the lens 2 and is placed between the lens 2 and the sample to act as a beam director 3. In this embodiment, the beam director 3 is polished on an angle to yield a prism effect. If the beam director 3 is then spun circumferentially, the beam transmitted through the single-mode optical fiber 1 will sweep out, or scan, a conical section. Such a scan can be useful for applications where the probe is adapted for use as an insertional medical device, such as a small guidewire, catheter, endoscope, bronchoscope, needle, or trocar.

Imaging Applications For Ultra-Small Optical Probes

The invention provides ultra-small optical probes which can be used to measure the optical properties of a test sample in situ. In one embodiment of the invention, shown in FIG. 8, the ultra-small optical probe is coupled to an optical system 16 and the probe is placed in proximity to a test sample(in this embodiment, a blood vessel 17). An optical beam is transmitted from the probe to the sample in situ; and light transmitted from the sample is detected. As defined herein, the term "in situ" means without removing the sample from its natural location and includes imaging internal vessels, spaces, or channels inside the body of a human being. As defined herein, the term "test sample" is used to refer to any sample for which measurements of optical properties are desired. The term "test" does not imply that the sample relates to a pathological condition or even that the optical properties of the sample are unknown; however, the probes and methods of the present invention may be used to diagnose and intervene in pathological conditions.

The invention also relates to connectors 12 and 15 which connect the ultra-small optical probes to optical beam delivery and imaging systems 16. The connectors allow the user to quickly connect and disconnect a probe from an optical imaging system 16, and in particular, from a driving mechanism which drives the optical probe to perform scanning of a sample. In one embodiment of the invention, the ultra-small optical probe comprises a housing 11 which is in the form of an insertional medical device and is used to image narrow, tortuous lumens or small spaces in situ within the body of an organism. Although medical applications are discussed further below, it should be clear to those of ordinary skill in the art that the ultra-small optical probes disclosed herein can be used to measure the optical properties of a variety of spaces (e.g., imaging channels or spaces in articles of manufacture) and that such applications are also encompassed within the scope of the present invention.

Figure 8:
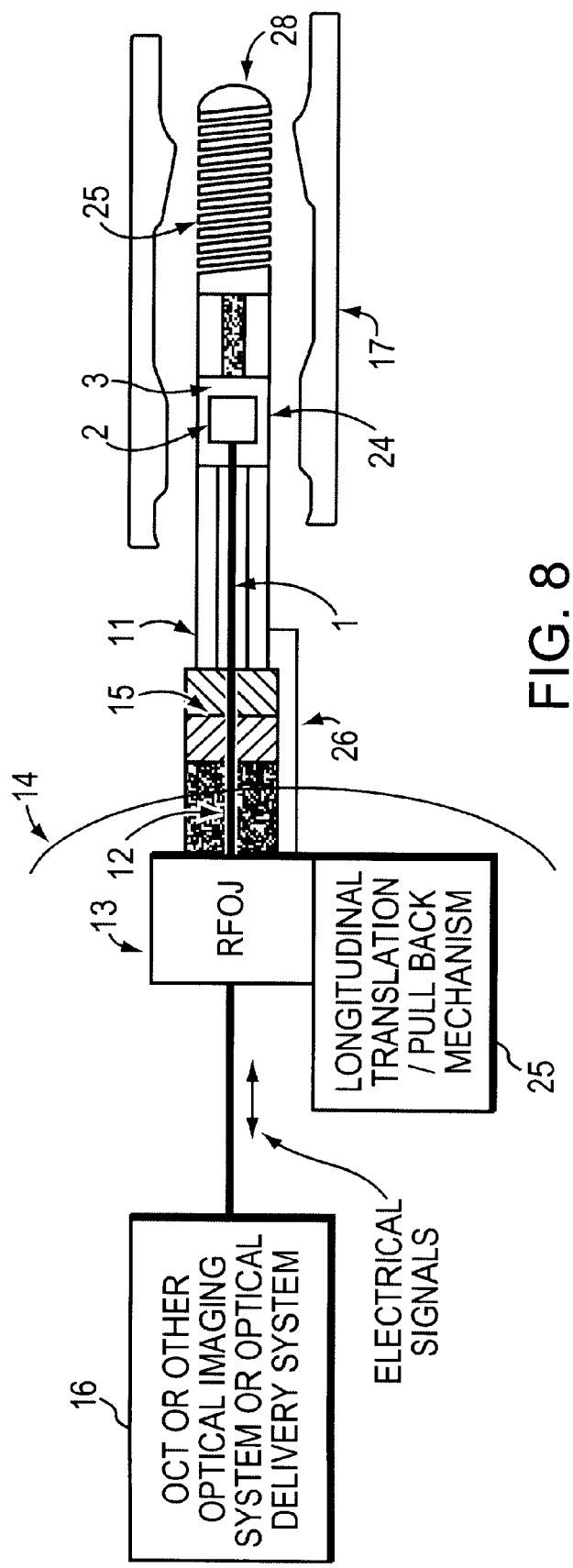
FIG. 8 shows an optical probe according to one embodiment of the invention where the probe includes a housing in the form of a guidewire.

In one embodiment of the invention, the ultra-small optical probe comprises a probe housing 11 which is in the form of an insertional medical device. FIG. 8 shows an embodiment of the invention in which the probe housing 11 is a guidewire. Other types of insertional medical devices are also contemplated, and are encompassed within the scope of the invention. These include, but are not limited to, bronchoscopes, needles, endoscopes and trocars. The guidewires of the present invention may also be used as components of other insertional medical devices (e.g., adapted for fitting into the guidewire lumen of a catheter). Guidewire housing 11 materials include, but are not limited to, metal, plastic, hypotubes, and the like.

In one embodiment of the invention shown in FIG. 8, the miniature optical fiber 1/optics lens 2/beam director 3 assembly of the ultra-small optical probe is housed inside a small guidewire housing 11 (typically <0.018″ in diameter). As shown, an OCT or other optical imaging or beam delivery system (e.g., a photodynamic therapy system or fluorescence system), is connected to the probe housing 11 via a rotatable fiber optic joint (RFOJ) 13 using detachable electrical connectors 12 and 15 and optical connectors (including single-mode fiber 1). The RFOJ 13 is used to circumferentially spin or rotate a single-mode fiber 1 or a miniature torque fiber within the probe housing 11. This device can be similar to the one described in U.S. Ser. No. 08/607,787, filed Feb. 27, 1996, the entire disclosure of which is herein incorporated by reference.

Single-mode fibers 1 used in this embodiment of the invention are those known in the art and typically consist of a ~4–10 $\mu$m core, a 80–125 $\mu$m cladding, and a 250–900 $\mu$m protective buffer. To minimize the diameter of the fiber 1 the protective buffer can be removed. Alternatively, the protective buffer can be replaced with a relatively thin (1 $\mu$m to 50 $\mu$m), high strength, low friction coating to fit within the small opening defined by of the optical probe housing 11. Such high strength coatings can be obtained from commercial fiber houses such as Corning® and Spectran®. Thus, the single-mode fiber 1 can be directly torqued to perform rotational scanning or a miniature torque cable can be added to aid in torching the fiber 1. It is important that the internal diameter of the guidewire housing 11 be made to have minimal friction and burrs.

In one embodiment of the invention, the output of the RFOJ 13 is connected to a disposable connector 12 that consists of an FC/APC male to female connector with minimal loss and back-reflections. In a further embodiment of the invention, disposable connector 12 is used to cross the sterile/non-sterile boundary 14. In another embodiment of the invention, the RFOJ 13, as well as the connector 12, are housed in a disposable sterile bag to allow repeated use of the RFOJ 13 by eliminating contaminants. The bag covers the RFOJ 13 and associated proximal coupling hardware to prevent any patient or sample bodily contaminants from touching the hardware. Thus, after a patient exam the bag can be removed and thrown away without the need to sterilize the RFOJ 13 and proximal coupling hardware. Such bags are standard in intravascular ultrasound devices and are required in such medical procedures by the Food and Drug Administration.

In one embodiment of the invention, the output of the disposable connector 12 is connected to a quick disconnect unit 15. The purpose of the quick disconnect unit 15 is to allow the physician/user to quickly disconnect both the guidewire housing 11 and another insertional or interventional medical instrument to which the guidewire housing 11 is coupled from the disposable connector 12 and RFOJ 13. The other insertional/interventional medical device is then passed over the guidewire housing 11 for interchange with still other devices or for manipulation by the physician/user. Insertional/interventional medical devices to which the guidewire housing 11 may be coupled include, but are not limited to, a pass or exchange catheter, a balloon angioplasty device, a stent delivery device, an artherectomy catheter, and a drug delivery device.

For example, if the physician is viewing an arterial lesion in a blood vessel 17 that he/she determines will require an interventional procedure, he/she quickly disconnects the guidewire housing 11 from the RFOJ 13 via the quick disconnect unit 15 (shown in FIGS. 8 and 9), slides a suitable interventional device over the guidewire, reconnects the housing 11 to the RFOJ 13, and begins imaging using imaging system 16. Using an imaging display output of the imaging system 16 physician/user can easily see when the interventional device is over the lesion. By being able to watch the placement of the interventional device during the interventional procedure the physician/user can inspect the lesion after the interventional device is removed.

In further embodiments of the invention, the physician uses the guidewire probe and the interventional device in an artherectomy procedure (or other surgical cutting procedure) where the optical probe allows the physician/user to determine where to cut. In a further embodiment of the invention, the interventional device used in conjunction with the guidewire probe is a drug delivery device where the image produced on a display screen of the optical system 16 allows the physician/user to determine how much of a drug to inject per unit time. In a further embodiment of the invention, the optical imaging system 16 used is an OCT system and the interventional device used is a stent. In this embodiment of the invention, the length and type of stent is determined before the procedure and the amount of inflation of the stent is controlled as the stent is being deployed, using information obtained from the optical probe and imaging system 16.

In the embodiment of the invention where the probe housing 11 is a guidewire, it is preferred that the diameter of that portion of the quick disconnect unit 15 which is adjacent to a first end of the guidewire housing 11 (the end closest to the disconnect unit 15) not exceed the maximum diameter of the guidewire housing 11 (e.g., 0.014 inches) to allow the easy exchange of other insertional/interventional devices over the guidewire housing 11.

Figure 9A:
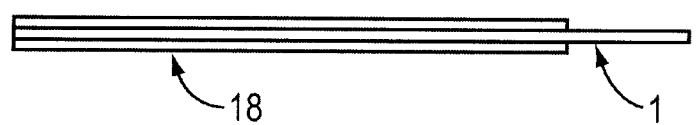
FIGS. 9A–C show views of a quick disconnect unit according to one embodiment of the invention.
Figure 9B:
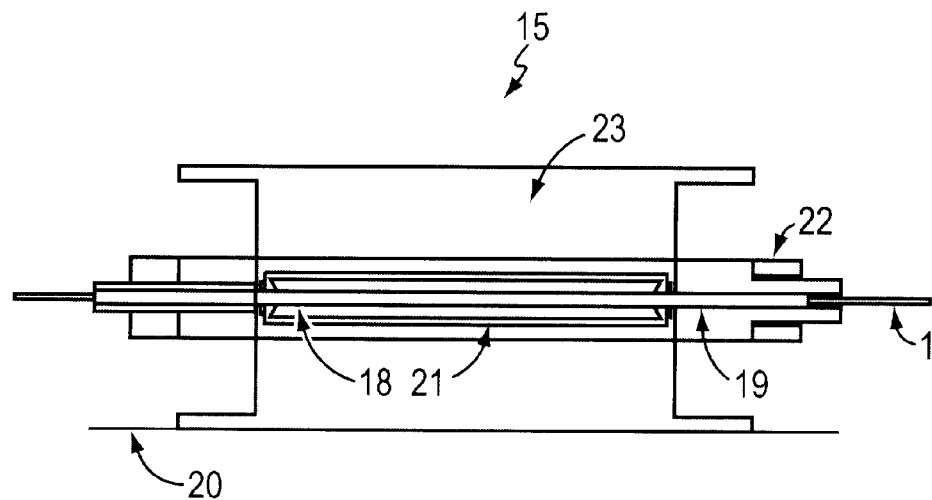
Figure 9C:
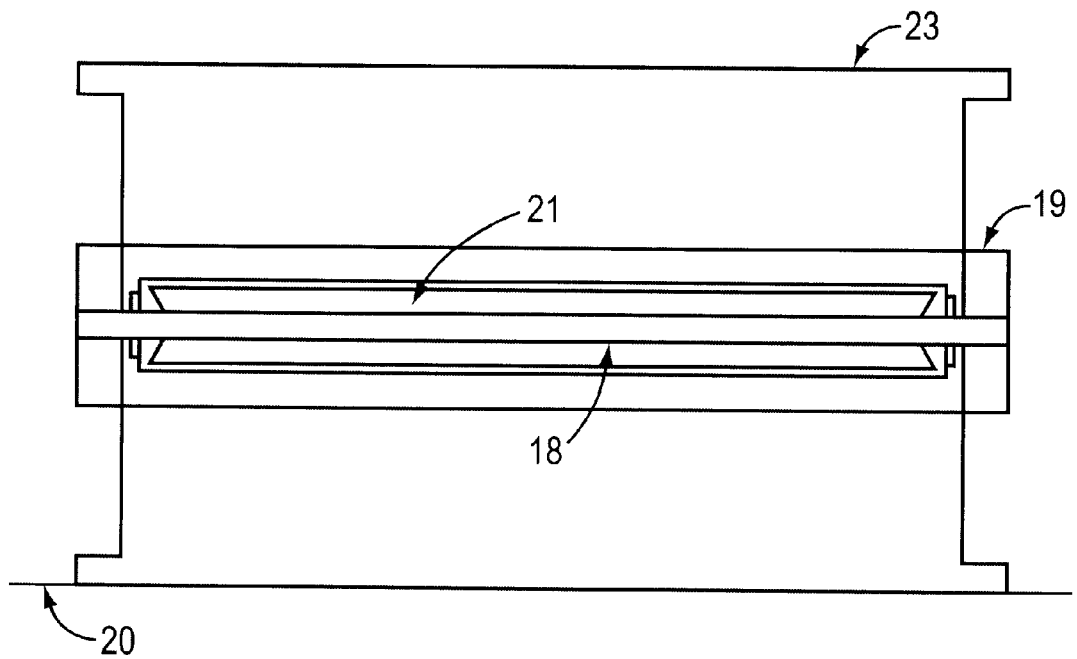

FIGS. 9A–C show the mechanical design of the quick disconnect unit 15 according to one embodiment of the invention. In this embodiment, a single-mode fiber 1 which is polished (or cleaved) at one end is contained within ferules 18 having a 0.014" outside diameter (FIG. 9A). The ferules 18 are generally tubular structures which can be made from a wide variety of materials including, but not limited to, ceramic, glass, metal and plastic. The ferules 18 are precision-manufactured to tight tolerances both diametrically and between the inside and outside diameters of the ferules 18 and the single-mode optical fiber 1/lens 2/mirror 3, to ensure proper alignment between these optical elements. For example, if the core diameter of the optical fiber 1 is ~5 $\mu$m, then the tolerance is less than 1 $\mu$m. To help alleviate the requirement for a tight tolerance, it is possible to use miniature lenses 2 similar to the lenses disclosed herein to increase the mode size of the fiber 1 and to collimate light between facets of the fiber 1. This would then allow a dramatic increase in the alignment tolerances required. A rough rule of thumb is that the alignment tolerance is approximately 10% of the beam diameter at the lens 2 facet. In a further embodiment of the invention, the ferule 18 is also keyed and angle-polished (as is done with commercial FC/APC connectors) to minimize back-reflections.

The polished single-mode optical fiber 1/lens 2/mirror 3/ferule 18 assembly is then fit within a ferule collar 19 (FIG. 9B). The ferule collar 19 is slit radially (the slit not visible on this scale drawing) to the center to facilitate side loading of the single-mode optical fiber 1/lens 2/mirror 3/ferule 18 assembly into the housing 23 of the quick disconnect unit 15. Slitting the components radially allows the single-mode optical fiber 1/lens 2/mirror 3/ferule 18 assembly to be quickly removed from the quick disconnect unit 15 to facilitate passage of an insertional/interventional medical device over the probe housing 11. In a further embodiment of the invention, an elastomeric spring 22 is provided at the end of the ferule collar 18 closest to the housing 23 of the quick disconnect unit 15.

The single-mode optical fiber 1/lens 2/mirror 3/ferule 18 assembly is set within an endcap 20 which is also radially slit (slit not visible in FIG. 10B) to the center. The endcap 20 is screwed into a split sleeve 21 contained within the housing 23 of the quick disconnect unit until it can no longer be turned. As the endcap 20 is being inserted, the ferules 18 are being pressed into the split sleeve 21. The split sleeve 21 is cut axially to allow for radial expansion. It is manufactured with a precision inside diameter that is slightly smaller than that of the ferules 18. The split sleeve 21 is contained sufficiently loosely within the housing 23 of the quick disconnect unit 15 allowing it to self-center itself. Interference created between the inside diameter of the split sleeve 21 and the outside diameter of the ferules 18 is used to align the ferules 18 radially and to maintain concentricity with the split sleeve 21, the end cap 20, and the ferule collar 19.

In the embodiment of the invention where an elastomeric spring 22 is provided in proximity to the ferule collar 19, fully engaging the endcap 20 compresses the elastomeric spring 22, applying an axial load that forces the ferules 18 containing the optical fiber 1 and the split sleeve 21 together. In one embodiment of the invention, the elastomeric spring 22 is split radially to the center. The axial force created by the compressed spring 22 and the precision radial alignment between the ferules 18 and split sleeve 21 creates a reliable optical connection between the optical elements of the ultra-small probe.

In a preferred embodiment of the invention, the probe housing 11 together with the portion of the connector device proximal to the probe housing 11 is not substantially greater in diameter than the outer diameter of a standard guidewire so that a physician/user can quickly disconnect the optical probe from the RFOJ 13 add exchange other medical devices over the probe housing 11 and connector elements. In a further embodiment of the invention, the split sleeve 21 and the housing 23 of the quick disconnect unit 15 are designed so that the distal side of the quick disconnect 15 (away from the optical imaging system 16) includes a 0.014 inch ferule 18, but the proximal side has a much larger ferule 18 (e.g., >1 mm). In this configuration, the quick disconnect unit 15 is compatible with standard commercially available fiber optical connectors.

In another embodiment of the invention, the RFOJ 13 is also coupled to a longitudinal translation/pull back device 25 as shown in FIG. 8. The purpose of the pull back device 25 is to permit longitudinal scanning of the lens 2/beam director 3 of the optical probe/guidewire. This can be accomplished by actuating the pull back mechanism 25 to move one of the guidewire housing 11 and the optical fiber 1 along a longitudinal axis of the optical fiber. Movement is effected by pulling back a mechanical linkage 26 which is coupled to the guidewire housing 11 and the RFOJ 13 as shown in FIG. 8. The linkage 26 can be made by several methods as known by those skilled in the art, such as by using linear stepper stages or coil winding technology.

In one embodiment of the invention, the ferules 18 and guidewire housing 11 are mechanically linked using standard techniques for affixing rotary joints as known in the art. In another embodiment of the invention, the optical fiber 1 is pulled back within the housing 11 of the guidewire. In this case, the quick disconnect unit 15 is modified to allow relative longitudinal motion between the single-mode optical fiber 1 and the guidewire housing 11. In a further embodiment of the invention, where the optical probe/guidewire is part of another insertional medical device, such as a catheter, the entire optical probe/guidewire may be pulled back. This prevents the guidewire from damaging a vessel 17 and allows easy repositioning of the optical probe/guidewire after pull back. Using the pull back option, the optical probe/guidewire/catheter/optical system may be used as a diagnostic catheter, mapping out potential areas of intervention for a cardiologist, for example.

In another embodiment of the invention, the RFOJ 13 is eliminated in favor of a high-speed longitudinal scanning mechanism, such as a galvanometer driven translation mechanism. This type of scanning mechanism uses a Galvonometer motor coupled to a linear ball-bearing slide which is in turn coupled to the optical fiber 1. The slide is coupled to the motor using a flexure that translates the rotational motion of the galvonometer into linear translation of the slide and optical fiber 1. The high-speed scanning mechanism is used to "push-pull" the fiber back and forth at high speed past a transparent section in the probe housing 11 (e.g., a window 24). Thus, a longitudinal image instead of a circumferential image is obtained. A galvanometer driven translation mechanism may be obtained from commercial sources (e.g., General Scanning, Incorporated, Watertown, Mass.).

It should be obvious those of skill in the art that there are other types of connector elements that can be used and these are encompassed within the scope of the invention. For example, in one embodiment of the invention, the quick disconnect unit 15 and the disposable connector 12 are separable elements, while in another embodiment of the invention the quick disconnect unit 15 and disposable connector 12 are part of a single connector device. In the latter embodiment, the output of the RFOJ 13 also has ferules 18 which are the same size as that of the quick disconnect 15 and directly connects to the quick disconnect housing 23 so that the disposable connector 12 and quick disconnect 15 are thereby integrated into one assembly.

Figure 10:
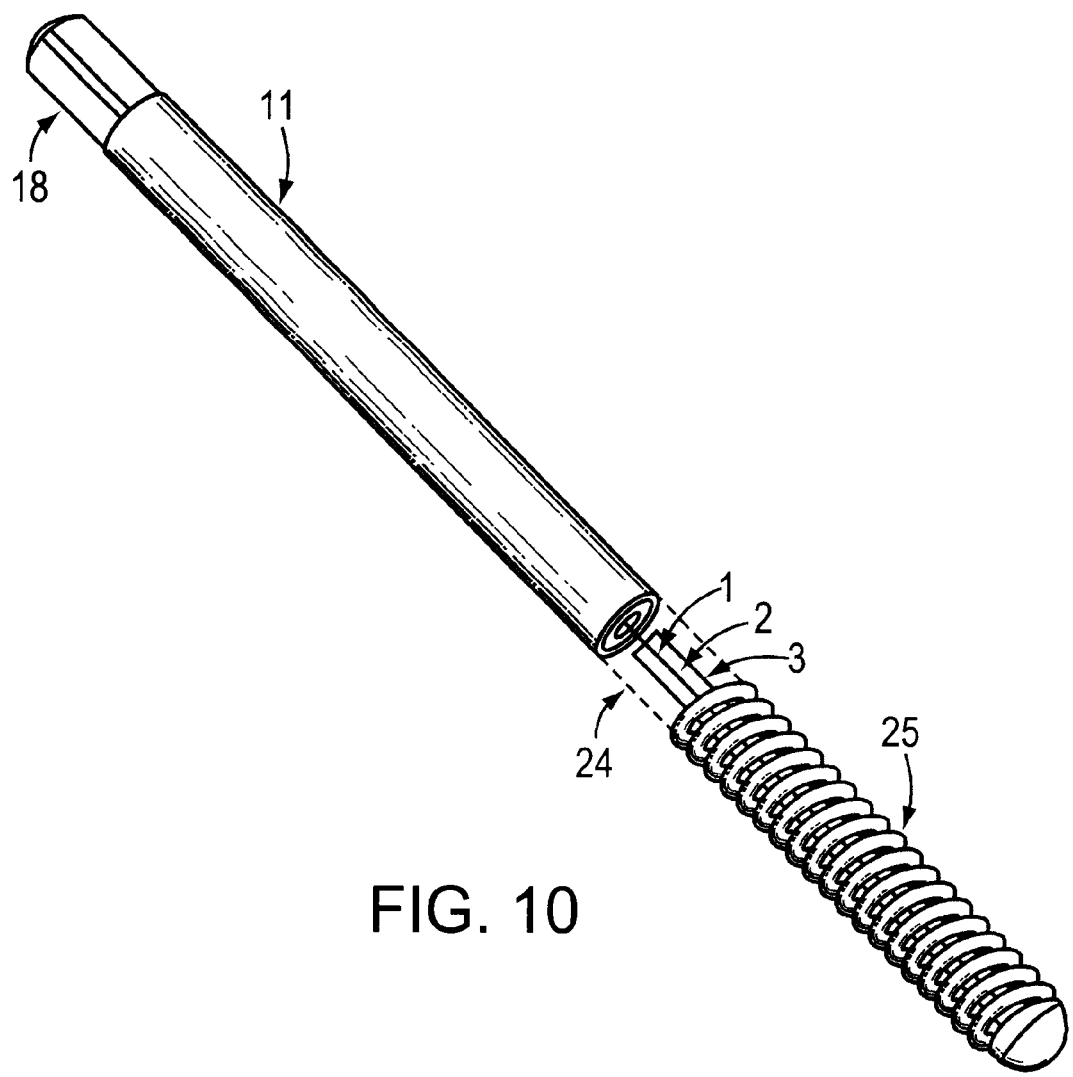
FIG. 10 shows an optical probe having a spring at the tip according to one embodiment of the invention and adapted for use as an imaging guidewire.
Figure 11A:
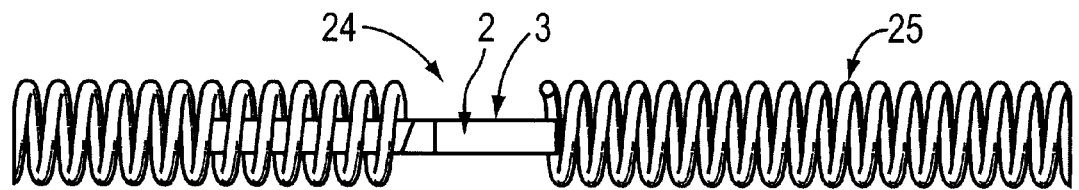
FIGS. 11A–C show an optical probe according to one embodiment of the invention in which the probe housing is covered by a spring.
Figure 11B:
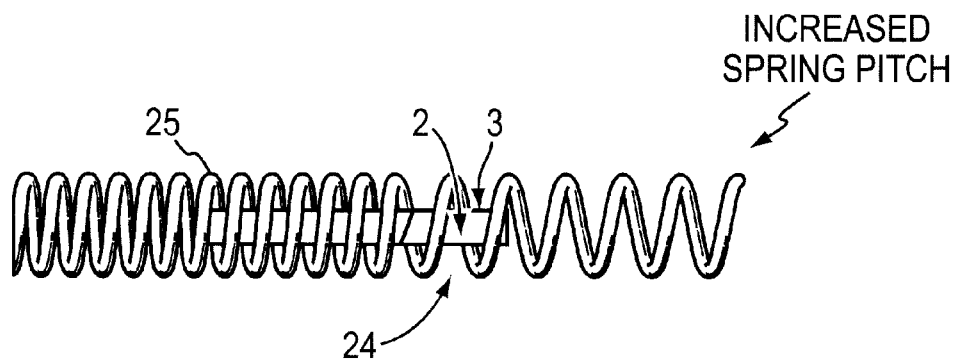
Figure 11C:
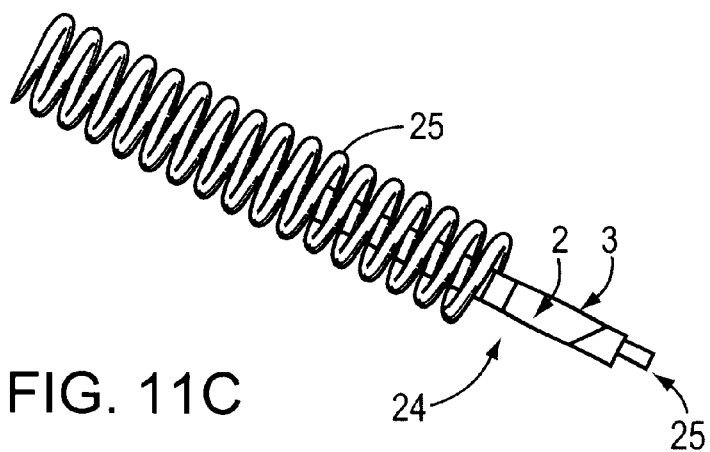
Figure 12:
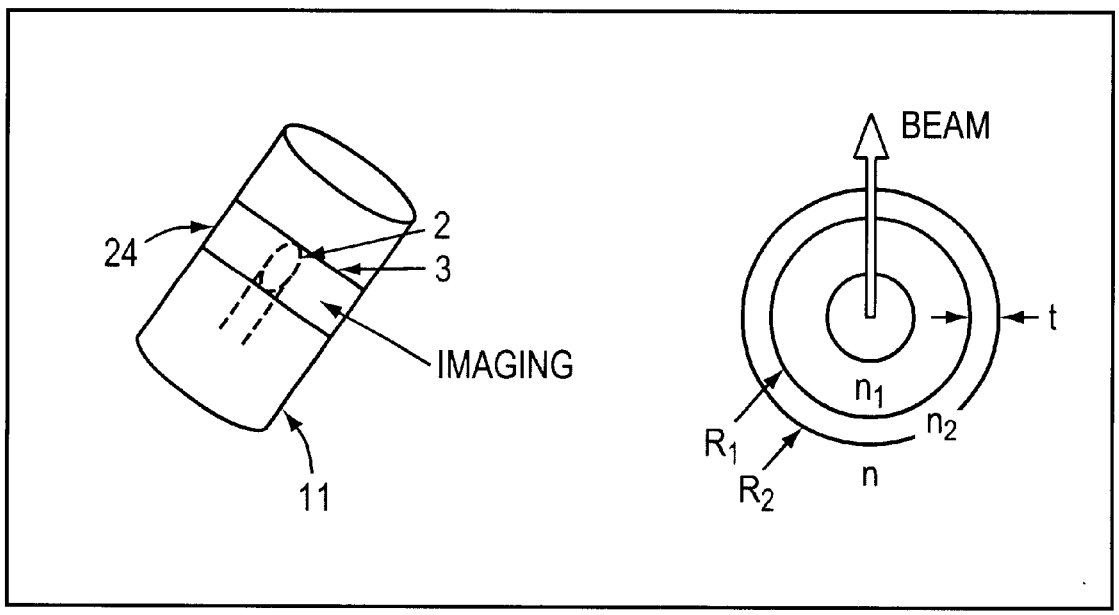
FIG. 12 shows a schematic diagram of a window in the housing of an optical probe according to one embodiment of the invention.

A guidewire housing 11 according to one embodiment of the invention is shown in more detail in FIG. 10. In this embodiment, the proximal end of the housing 11 mates with the quick disconnect unit 15. In one embodiment of the invention, the optical fiber 1 is free to spin relative to the housing 11 but is fixed longitudinally so that the quick disconnect ferule 18 and housing 11 cannot be separated. The combination of circumferential scanning from the spinning fiber 1 within the guidewire housing 11, and longitudinal scanning when the pull back mechanism 25 is used, allows a three-dimensional profile of a vessel 17 to be collected. Using the optical system 16, an image can be displayed and manipulated to allow the physician/user to view the vessel 17 on the imaging system's display monitor.

The probe housing 11 is fabricated so as to transmit light from the single-mode optical fiber 1 through at least a section of the housing 11 to the sample. Similarly, light retroreflected from the sample also passes through at least a section of the housing 11 back to the single-mode optical fiber 1. Thus, in a preferred embodiment of the invention, a section of the housing 11 is at least partially transparent.

In one embodiment of the invention where probe housing 11 is in the form of a guidewire, the housing 11 includes an opening 24, such as a window, which is in optical communication with the lens 2 and beam director 3. The opening/window 24 is secured in the housing 11 wall to allow the lens 2/beam director 3 to image through the guidewire housing 11 and onto the sample (e.g., a blood vessel 17 wall). In a further embodiment of the invention, the beam director 3 is in proximity to a section of the housing 11 which is at least partially transparent, e.g., the opening/window 24. In another embodiment of the invention, the housing 11 itself is made of plastic or another suitable material that may be transparent to optical radiation. In this embodiment of the invention, no opening or window 24 is needed. In a further embodiment, the housing 11 may comprise a hole (e.g., a slot, a notch, a port, a cutout), or a plurality of holes, through which the beam from the single-mode optical fiber 1 may be directed for scanning of the sample. As defined herein an "opening" may be uncovered and completely open or may be covered by a transparent material.

The design of the opening/window 24 (in FIGS. 8, 10, and 11A–C) is an important part of the overall optical probe design. The window 24 allows light from an optical fiber 1 to be transmitted through the housing wall 11. Using standard precision machining and joining technologies, it is possible to incorporate suitable window 24 materials into the housing 11. Windows 24 that are formed into transparent tubes that exhibit the same or similar outside diameter and shape as the primary housing 11 are greatly preferred since they are easiest to join to the housing 11. This ensures that the completed assembly does not exhibit any sharp edges or discontinuities, a critical consideration in medical applications. Flat window 24 materials can be used, as discussed above with respect to the metering tubing 9. While flat window 24 materials make the optical imaging properties of the probe easier to deal with, flat windows cannot be made to accommodate 360 degree scanning and therefore cannot be used when a circumferential scanning guidewire optical probe is desired.

If circular/cylindrical windows 24 are chosen, consideration must be given to the effects of the window 24 material and window 24 shape on the quality of the image that the probe can produce. Standard equations from classical optics give a good insight into the nature of the problems encountered (FIG. 13):

$$\frac{n_1}{f_1} = \frac{n_2}{f_2} = \frac{n_2 - n_1}{R_1} - \frac{n_2 - n_3}{R_2} + \frac{(n_2 - n_3)(n_2 - n_1)t}{n_2 R_1 R_2} \quad (9)$$

where $n_1$ is the medium index to the left of the window 24, $n_2$ is the index of the window 24 material itself, $n_3$ is the index in the medium to the right of the window 24, $R_1$ is the inner radius of curvature, $R_2$ is the outer radius, and $t$ is the window 24 thickness. It becomes apparent from examining the above equation that to minimize the effects of the window 24 which could lead to poor image quality (i.e., by driving the focal lengths $f_1$ and $f_2$ towards $\infty$), the most important issue is matching the three indices, followed by decreasing the thickness of the window 24 material. Decreasing the thickness of the window 24 material also drives the inner and outer radius of curvature closer, further minimizing the cylindrical focusing effects of a window having a curved surface by equalizing the radius of curvatures.

It is understood that the above equation is for a window with a spherical surface, whereas when using the circular/cylindrical windows of the present invention, the effect is only in the direction parallel to the housing 11 axis. However, the above equation serves to illustrate the importance of matching the index of refraction of the window 24 with that of the medium to obtain better image quality.

A flat window 24 (i.e. driving the radii towards $\infty$) will also minimize detrimental effects on imaging. In a further embodiment of the invention, a window 24 section is made in a square or hexagonal form to allow radial scanning of a sample. In this embodiment, as the flat window 24 would still distort the scanning of the beam, a scan correction algorithm is programmed into a processor which is part of the optical system 16. Thus, circular windows are preferred. Window 24 materials which possess desired qualities (index, material strength, optical transmission, material optical quality, sterilizability, and so forth) include, but are not limited to, fluoropolymers, other plastics, glass, and the like.

In a further embodiment of the invention, a series of small holes are provided in the proximal section of the housing 11 wall to allow the outside sample medium (e.g., water or saline) to fill any interstitial gaps between the lens 2, beam director 3, and the inner radius of the window 24, to further aid in index-matching and to reduce unwanted Fresnel reflections. In a further embodiment of the invention, the space between the lens 2 and the window 24 is filled and sealed with an optical transmitter including a gel, an oil, or other suitable materials, to perform the desired refraction index matching.

Choosing the proper index-matching fluid can be accomplished using the following relationship:

$$\frac{n_2 - n_1}{R_1} = \frac{n_2 - n_3}{R_2} \quad (10)$$

where the parameters are as given above. Here $n_1$ is the index of the matching fluid or gel, $n_2$ is the index of the window 24 material, and $n_3$ is the index of refraction of the surrounding sample medium. Given that the window 24 dimensions and index of refraction are fixed, choosing the matching material according to the above relationship will effectively neutralize the optical effects of the window 24 to first order.

In a one embodiment of the invention, the index-matching material is placed in the optical probe/guidewire just prior to patient use. Gaussian beam modeling, as previously described, can be employed to more accurately assess the effect of a curved window 24 on image quality, allowing engineering design decisions to be made when choosing materials and shapes. Finally, it is possible to eliminate any window altogether by simply providing a series of slots or holes in the housing 11 wall. In this embodiment, the larger the fraction of holes in the housing 11 wall (e.g., a hypotube), the larger the fraction scan area. The number of holes in the housing 11 is optimized to maximize image quality while maintaining structural integrity.

The probe housing 11 may further comprise elements found in standard guidewires. In one embodiment (FIG. 10), a spring 25 is affixed to the opening/window 24 of the guidewire housing 11. The spring 25 allows the optical probe/guidewire flexibility in navigating tortuous pathways in the body. The spring 25 is configured so as not to cover at least a section of the housing 11 which includes the opening/window 24. In a further embodiment of the invention (FIGS. 11A–C), the opening 24 comprises a clear section of hypotube and two sets of springs 25 are provided; each set stopping short of the opening 24/hypotube. In one embodiment, a flat safety ribbon is used to ensure that both ends of the spring coil 25 remain attached. In another embodiment of the invention, the spring 25 can be continually wound to be one unit. The opening 24/hypotube is affixed to both ends of the spring with an adhesive or by mechanical means. Safety ribbons can also be used. In another embodiment of the invention, the spring 25 includes a radio-opaque tip 28. In a further embodiment of the invention, the entire spring 25 comprises radio-opaque material. By providing a radio-opaque tip 28 or radio-opaque material, the passage of the optical probe/guidewire through a lumen is easily visualized using an angiography monitor, for example.

In another embodiment of the invention, a mechanism to flush sample medium (e.g., blood) from the optical probe/guidewire is provided in order to improve the penetration depth of the image. In one embodiment of the invention, flushing is done automatically using the optical system 16 (e.g., an OCT system) or manually, using standard flushing catheters passed over, or adjacent to, the guidewire housing 11.

Although a guidewire is shown and discussed in FIGS. 8–11A–C, it is clear that the lens 2 technology and scanning mechanisms described with respect to the Figures can be used for a wide range of other medical (and non-medical) probes such as miniature catheters, endoscopes, bronchoscopes, needles, and trocars.

Having thus described certain embodiments of the present invention, various alterations, modifications, and improvements will be apparent to those skilled in the art. Such variations, modifications and improvements are intended to be within the spirit and scope of the invention. Accordingly, the foregoing description is by way of example only and is not intended to be limiting.

What is claimed is:

1. An optical imaging probe comprising:
a single-mode optical fiber including a core having a first diameter and a cladding layer having a second diameter, the single-mode optical fiber conveying an optical beam at the first diameter; and
a graded index optical fiber fixedly and optically coupled to the single-mode optical fiber and having substantially the same diameter as the second diameter of the cladding layer, the graded index optical fiber expanding the optical beam from the first diameter to a desired diameter while traversing the graded index optical fiber and focusing the optical beam to form a spot size smaller than 100 µm in diameter at a working distance greater than 1 mm from an end of the graded index optical fiber.

2. The optical imaging probe of claim 1 further comprising a beam director fixedly and optically coupled to the graded index optical fiber, the beam director including a coating to selectively convey the optical beam at a predetermined wavelength.

3. The optical imaging probe of claim 1 further comprising a beam director fixedly and optically coupled to the graded index optical fiber, the graded index optical fiber adapted to account for the optical effects of the beam director.

4. The optical imaging probe of claim 1 further comprising a beam director fixedly and optically coupled to the graded index optical fiber, wherein the beam director includes a coreless fiber polished at an angle.

5. The optical imaging probe of claim 1 further comprising a beam director fixedly and optically coupled to the graded index optical fiber, the beam director directing the optical beam from a reflective surface at an end thereof to a flat transmissive surface along a length thereof.

6. The optical imaging probe of claim 1 further comprising:
a beam director optically coupled to the graded index optical fiber; and
a housing defining a bore therein for receiving the single-mode optical fiber, graded index optical fiber, and beam director, the housing including a section at least partially transparent to the optical beam.

7. The optical imaging probe of claim 6 further comprising:
an optical transmitter stored within the housing and positioned between the beam director and the at least partially transparent section of the housing, the optical transmitter adapted to neutralize an optical effect of the at least partially transparent section of the housing.

8. A method of measuring the optical properties of a test sample in situ, the method comprising the steps of:
providing a single-mode optical fiber including a core having a first diameter and a cladding layer having a second diameter, the single-mode optical fiber being adapted to convey an optical beam at the first diameter;
providing a graded index optical fiber fixedly and optically coupled to the single-mode optical fiber and having substantially the same diameter as the second diameter of the cladding layer;
transmitting the optical beam at the first diameter to the graded index optical fiber via the single-mode optical fiber;
expanding the optical beam from the first diameter to a desired diameter while traversing the graded index optical fiber;
focusing, by the graded index optical fiber, the optical beam to form a spot size smaller than 100 µm in diameter at a working distance greater than 1 mm from an end of the graded index optical fiber, the working distance corresponding to a location of the test sample in situ; and
detecting light reflected back from the test sample.

9. The method of claim 8 further comprising the steps of:

determining the optical properties of the test sample from the light reflected therefrom; and comparing the optical properties of the test sample to optical properties of a control sample.

10. The method of claim 8 further comprising the steps of:

providing a beam director fixedly and optically coupled to the graded index optical fiber; and compensating, by the graded index optical fiber, for the optical effects of the beam director.

11. The method of claim 10 further comprising the steps of:

inserting the single-mode optical fiber, graded index optical fiber, and beam director within a bore defined by a housing; and transmitting the focused optical beam through an optical transmitter located between the beam director and the housing, the optical transmitter neutralizing an optical effect associated with a transparent section of the housing.

* * * * *